US009630953B2

(12) United States Patent
Yao et al.

(10) Patent No.: US 9,630,953 B2
(45) Date of Patent: Apr. 25, 2017

(54) SMALL COMPOUNDS TARGETING TACC3

(71) Applicant: JAPANESE FOUNDATION FOR CANCER RESEARCH, Tokyo (JP)

(72) Inventors: Ryoji Yao, Tokyo (JP); Hiroyuki Osada, Saitama (JP); Yasumitsu Kondoh, Saitama (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 0 days.

(21) Appl. No.: 14/398,301

(22) PCT Filed: Apr. 30, 2013

(86) PCT No.: PCT/JP2013/062674
§ 371 (c)(1),
(2) Date: Oct. 31, 2014

(87) PCT Pub. No.: WO2013/165008
PCT Pub. Date: Nov. 7, 2013

(65) Prior Publication Data
US 2015/0111888 A1    Apr. 23, 2015

(30) Foreign Application Priority Data
May 2, 2012    (JP) ................................ 2012-104997

(51) Int. Cl.
C07D 309/30    (2006.01)
C07D 405/14    (2006.01)
C07D 401/14    (2006.01)
C07D 311/16    (2006.01)
A61K 31/37    (2006.01)
A61K 31/4025    (2006.01)
A61K 31/5377    (2006.01)
C07D 403/14    (2006.01)
C07D 407/04    (2006.01)
A61K 31/4409    (2006.01)
A61K 31/445    (2006.01)
A61K 31/4465    (2006.01)

(52) U.S. Cl.
CPC ............ *C07D 405/14* (2013.01); *A61K 31/37* (2013.01); *A61K 31/4025* (2013.01); *A61K 31/445* (2013.01); *A61K 31/4409* (2013.01); *A61K 31/4465* (2013.01); *A61K 31/5377* (2013.01); *C07D 311/16* (2013.01); *C07D 401/14* (2013.01); *C07D 403/14* (2013.01); *C07D 407/04* (2013.01)

(58) Field of Classification Search
CPC .............................. A61K 31/37; C07D 405/14
USPC ....................................................... 549/263
See application file for complete search history.

(56) References Cited

FOREIGN PATENT DOCUMENTS

JP     2009-167163    7/2009
JP     2012-005479    1/2012
WO     2005/071419    8/2005

OTHER PUBLICATIONS

West (Solid-State Chemistry and Its Applications, 1984, John Wiley & Sons).*
Frasinyuk, Chemistry of Heterocyclic Compounds (New York, NY, United States) (2012), 48(3), 422-426.*
International Search Report, Date of mailing: Jul. 16, 2013 (Jul. 16, 2013).
Chemistry of Heterocyclic Compounds, vol. 48 No. 3—Jun. 2012, (Khimiya Geterotsiklicheskikh Soedinenii), Listed in International Search Report, English text.
Chemistry of 3-H Etarylcoumarins 3*.Synthesis and Aminomethylation of 7'-Hydroxy-3,4'-Bicoumarins, M.S. Frasinyuk et al., Chemistry of Heterocyclic Compounds, vol. 48, No. 3, Jun. 2012, Listed in International Search Report, English text.
Identification of Novel Human Dipeptidyl Peptidase-IV Inhibitors of Natural Origin (Part I): Virtual Screening and Activity Assays, Laura Guasch et al, Sep. 2012, vol. 7, Issue 9, Listed in International Search Report, English text.
Microtubules and resistance to tubulin-binding agents, Maria Kavallaris, Nature Reviews/Cancer, vol. 10, Mar. 2010, Discussed in specification, English text.
Targeting Mitosis for Anti-Cancer Therapy, Valery and Timothy J. Yen, Developments in Cancer Therapy, Discussed in specification, English text.
Characterization of the cDNA and pattern of expression of a new gene over-expressed in human hepatomas and colonic tumors, Sophie Charrasse et al., Discussed in specification, English text.
A sequence variant at 4p16.3 confers susceptibility to urinary bladder cancer, Lambertus A. Kiemeney et al., Nature Genetics, vol. 42, No. 5, May 2020, Discussed in specification, English text.
Cancer Epidemiology, Biomarkers & Prevention, Comparative Gene Expression Analysis of Ovarian Carcinoma and Normal Ovarian Epithelium by Serial Analysis of Gene Expression, David G. Peters et al., Discussed in specification, English text.
Gene expression profiles of human breast cancer progression, Xiao-Jun Ma et al., Discussed in specification, English text.
Transforming acidic coiled-coil 3 and Aurora-A interact in human thyrocytes and their expression is deregulated in thyroid cancer tissues, Salvatore Ulisse et al., Endocrine-Related Cancer (2007), Discussed in specification, English text.
The Third Member of the Transforming Acidic Coiled Coil-Containing Gene Family, TACC3, Maps in 4p16, Close to Translocation Breakpoints in Multiple Myeloma, and is Upregulated in Various Cancer Cell Lines, Ivan H. Still et al., Discussed in specification, English text.

(Continued)

*Primary Examiner* — Nizal Chandrakumar
(74) *Attorney, Agent, or Firm* — Rankin, Hill & Clark LLP

(57) ABSTRACT

The present invention provides a small compound targeting at TACC3. The present invention further provides a drug, particularly, an anticancer agent, comprising the small compound targeting at TACC3. A compound represented by the general formula (I) or a pharmaceutically acceptable salt, solvate, or ester derivative thereof binds to TACC3 and inhibits cell growth. Thus, these compounds can be used as drugs, particularly, anticancer agents.

6 Claims, 11 Drawing Sheets

(56) References Cited

OTHER PUBLICATIONS

TACC3 depletion sensitizes to paclitaxel-induced cell death and overrides p21(WAF)-mediated cell cycle arrest, L. Schneider et al., Oncogene (2008), Discussed in specification, English text.

Genes&Development, The ch-TOG/XMAP215 protein is essential for spindle pole organization in human somatic cells, Fanni Gergely et al., Discussed in specification, English text.

The TACC proteins: TACC-ling microtubule dynamics and centrosome function, Isabel Peset and Isabelle Vernos, Discussed in specification, English text.

Disruption of Tacc3 function leads to in vivo tumor regression, R. Yao et al., Onocogene (2012), Discussed in specification, English text.

The Application of the Chemical Array for Biological Study, Isao Miyazaki et al., Discussed in specification, English text.

Modified Coumarins. 14. Synthesis of 7-Hydroxy-[4.3']Dichrimenyl-2.2'-Dione Derivatives, I. P. Dubovik et al., Chemistry of Natural Compounds, vol. 40, No. 5, 2004, Discussed in specification, English text.

Panel of human cancer cell lines provides valuable database for drug discovery and bioinformatics, Takao Yamori, Cancer Chemother Pharmacol (2003), Discussed in specification, English Text.

European Search Report dated Mar. 11, 2016.

Modified Columarins. 14. Synthesis of 7-Hydroxy-[4,3]Dichromenyl-2,2'-Dione Derivatives, L.P. Dubovik, M.M. Garazd, and V.P. Khilya, Chemistry of Natural Compounds, vol. 4, No. 5, 2004.

Cytotoxic mechanisms of anti-tumour quinones in parental and resistand lymphoblasts, A. Halinska, T. Belej and PJ D'Brien, British Journal of Cancer [1996].

International Search Reort dated Jul. 16, 2013.

\* cited by examiner

SMALL COMPOUNDS TARGETING TACC3

TECHNICAL FIELD

The present invention relates to a small compound targeting at TACC3. The present invention also relates to a drug, particularly, an anticancer agent, based on the small compound targeting at TACC3.

BACKGROUND ART

Microtubules constitute spindles formed during cell division. Since tumor cells are in active cell division, agents inhibiting cell division are effective as anticancer agents. For this reason, anticancer agents targeting microtubules as the main structure of spindles or tubulin as a constituent protein thereof have been classically developed and used in treatment regardless of solid tumor or hematological tumor.

In fact, many compounds, such as vincristine and paclitaxel, which target microtubules, are widely used as anticancer agents. These agents are considered to exert their anticancer effects as a result of inhibiting spindle formation in tumor cells and thereby suppressing cell division.

These compounds, however, are known to cause serious adverse reactions such as peripheral neuropathy, because they target not only microtubules in spindles but microtubules in normal cells (e.g., Patent Literature 1 and Non Patent Literature 1). Also, particular isoforms of tubulin have been reported to have resistance to anticancer agents. It has been therefore required to develop a novel drug selectively targeting microtubules in tumor cells (Non Patent Literature 2).

In search for a compound selectively targeting microtubules in tumor cells, the present inventors have conducted analysis by focusing on TACC3, which are reportedly involved in microtubular polymerization and abnormally expressed in various tumors.

A gene encoding the TACC3 (transforming acidic coiled-coil 3) protein is considered to be a so-called cancer gene (e.g., Non Patent Literatures 3 to 8 and Patent Literature 2). TACC3 is also known to participate in spindle formation or the control of a mitotic apparatus involved in chromosome partitioning and cell division (e.g., Non Patent Literature 9). In addition, TACC3 and TOGp (tumor over-expressed gene) known to interact with TACC3 are overexpressed in various cancers.

The suppression of TACC3 expression induces different phenomena depending on the cell line used. For example, reduction in microtubular polymerization (Non Patent Literature 10) and apoptosis induced by chromosomal imbalance (Non Patent Literature 9) are reportedly observed.

These phenomena are explained, on the basis of findings obtained in *Xenopus* or *Drosophila*, by models in which TACC3 binds to TOGp and stabilizes microtubular polymerization in centrosomes during mitosis, thereby controlling cell division (Non Patent Literature 11).

The present inventors have experimented the suppression of TACC3 expression using TACC3-conditional knockout mice. As a result, the present inventors have found that lymphoma undergoes regression due to apoptosis, whereas normal thymus cells are found to express TACC3, but are not evidently affected thereby (Non Patent Literature 12). Thus, the present inventors have considered that compounds targeting at TACC3 may serve as excellent anticancer agents selectively acting on tumor cells, and already disclosed a method for screening for an anticancer agent targeting at TACC3 (Patent Literature 3).

CITATION LIST

Patent Literature

Patent Literature 1: Japanese Patent Laid-Open No. 2009-167163
Patent Literature 2: International Publication No. WO 2005/071419
Patent Literature 3: Japanese Patent Laid-Open No. 2012-5479

Non Patent Literature

Non Patent Literature 1: Kavallaris, M., Nat. Rev. Cancer (2010), 10, 194-204
Non Patent Literature 2: Sudakin, V. and Yen, T. J., BioDrugs (2007), 21, 225-33
Non Patent Literature 3: Charrasse, S. et al., Eur. J. Biochem. (1995), 234 (2), 406-413
Non Patent Literature 4: Kiemeney, L. A. et al., Nat. Genet. (2010), 42 (5), 415-419
Non Patent Literature 5: Peters, D. G. et al., Cancer Epidemiol. Biomarkers Prev. (2005), 14 (7), 1717-1723
Non Patent Literature 6: Ma, X. J. et al., Proc. Natl. Acad. Sci. USA (2003), 100 (10), 5974-5979
Non Patent Literature 7: Ulisse, S. et al., Endocr. Relat. Cancer (2007), 14 (3), 827-837
Non Patent Literature 8: Still, I. H. et al., Genomics (1999), 58 (2), 165-170
Non Patent Literature 9: Schneider, L. et al. Oncogene (2008), 27 (1), 116-125
Non Patent Literature 10: Gergely, F. et al. Genes Dev. (2003), 17, 336-341
Non Patent Literature 11: Peset, I., and Vernons, I. Trends Cell Biol. (2008), 18 (8), 379-388
Non Patent Literature 12: Yao, R. et al., Oncogene (2012), 31, 135-148
Non Patent Literature 13: Miyazaki, I. et al., Methods Mol. Biol. (2010) 669,95-107
Non Patent Literature 14: Dubovic I. P. et al., Chemist. Natural Compounds, (2004) 40, 434-443
Non Patent Literature 15: Yamori, T., Cancer Chemother. Pharmacol., (2007), 52 Suppl. 1, S74-79

SUMMARY OF INVENTION

Problems to be Solved by the Invention

An object of the present invention is to provide a small compound targeting at TACC3. Another object of the present invention is to provide a drug, particularly, an anticancer agent, comprising the small compound targeting at TACC3 and a method for producing the same.

Means for Solving the Problems

The anticancer agent of the present invention comprises a compound represented by the general formula (I) given below or a pharmaceutically acceptable salt, solvate, or ester derivative thereof as an active ingredient.

[Formula 1]

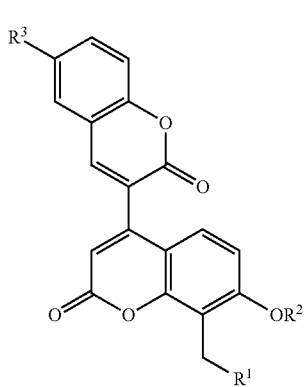

(I)

wherein R¹ represents

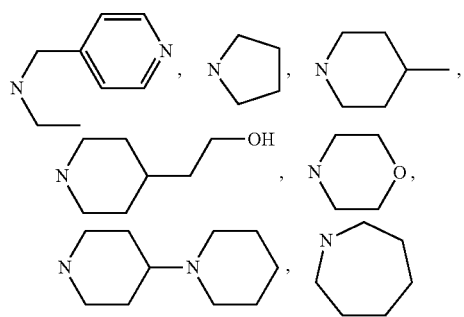

OAc, NEt$_2$, NMe(CH$_2$CH$_2$OH), NH(CH$_2$CH$_2$NMe$_2$), NEt(CH$_2$CH$_2$NMe$_2$), N(CH$_2$CH$_2$OMe)$_2$, N$^+$O$^-$(CH$_2$CH$_2$OMe)$_2$, NMe(CH$_2$)$_3$Me, or N(CH$_2$CH$_2$Me)$_2$; R² represents Ac or H; and R³ represents H, Cl, F, or Br.

The present inventors have revealed, by experiments using mice or cultured cells, that the above-mentioned compound having a dicoumarin structure suppresses cell division via TACC3 and exhibits an antitumor effect. Thus, effective anticancer agents can be developed by using these compounds as active ingredients for the anticancer agents. Anticancer agents selectively acting on tumor cells can be produced by using these compound in the treatment of a cancer expressing TACC3 and preparing these compounds into anticancer agent compositions.

The anticancer agent of the present invention comprises a compound of the general formula (I) represented by the following formula:

RT-002

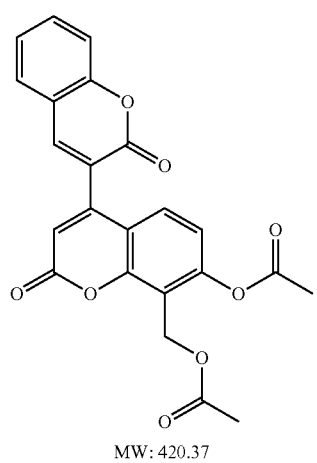

MW: 420.37

RT-003

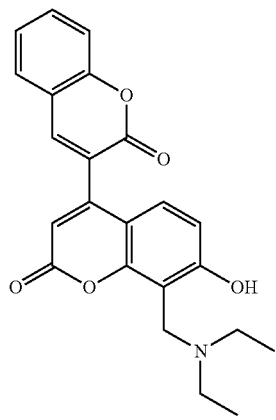

MW: 391.42

RT-004

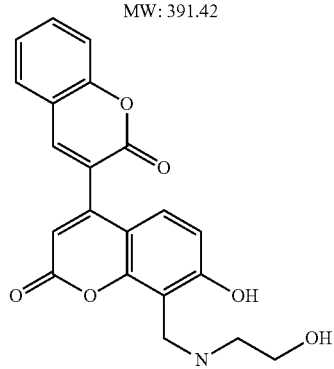

MW: 393.39

RT-005

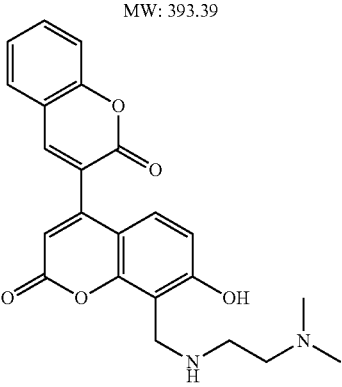

MW: 406.43

RT-006

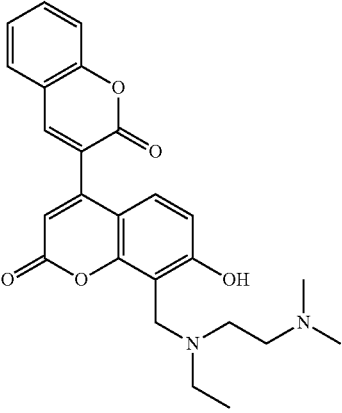

MW: 434.48

RT-007
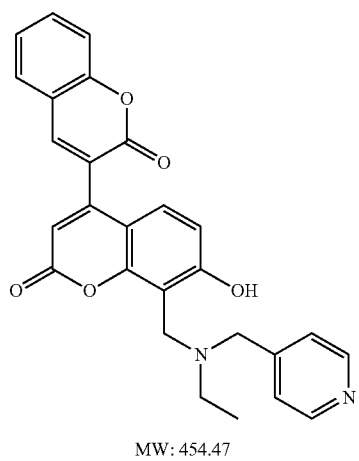
MW: 454.47
RT-008
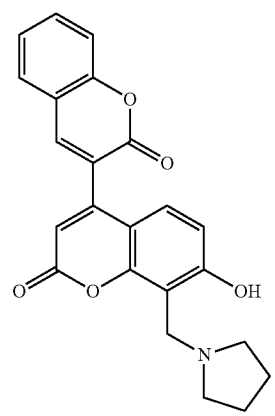
MW: 389.40
RT-009
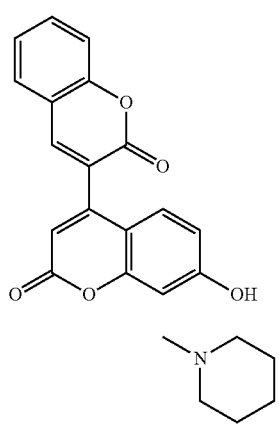
MW: 403.43
RT-0010
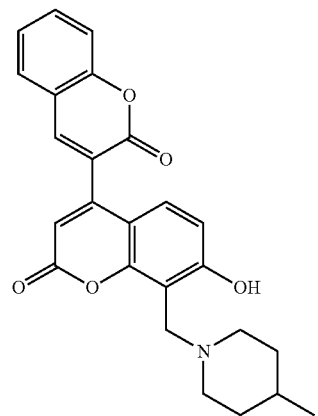
MW: 417.45
RT-011
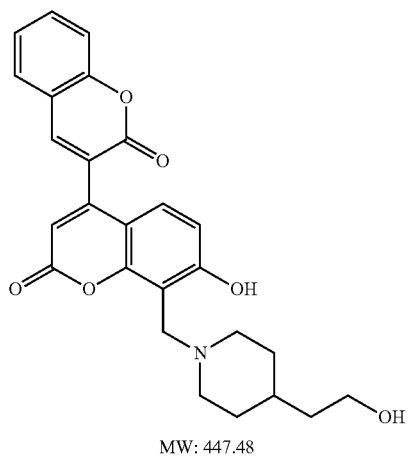
MW: 447.48
RT-012
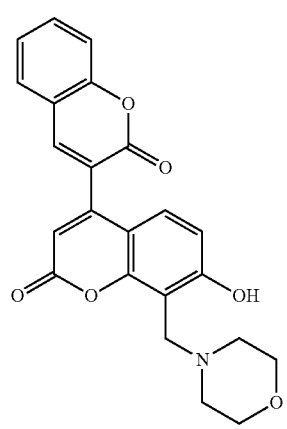
MW: 405.40

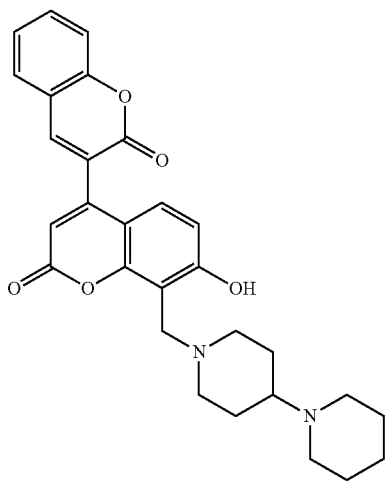
RT-0014
MW: 486.56
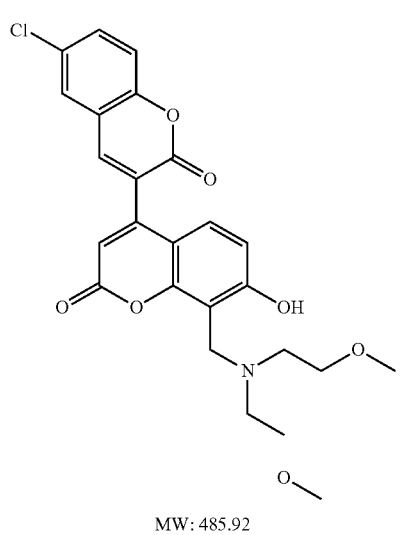
RT-0016
MW: 485.92
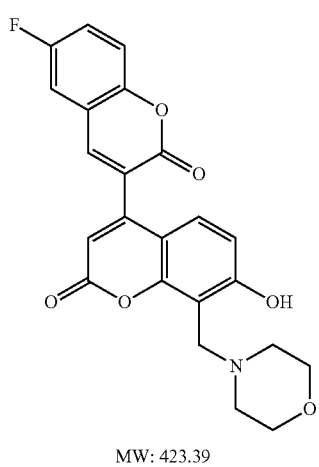
RT-0019
MW: 423.39
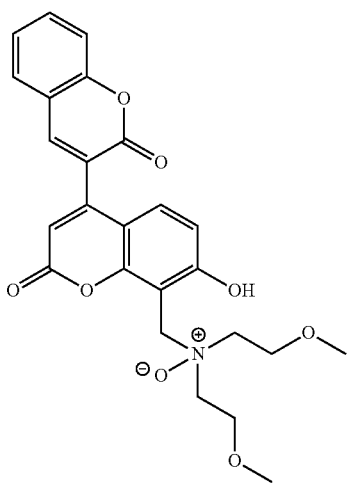
RT-0027
MW: 467.47
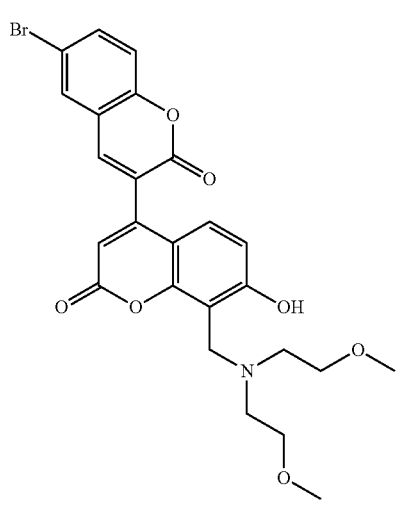
RT-0028
MW: 530.36
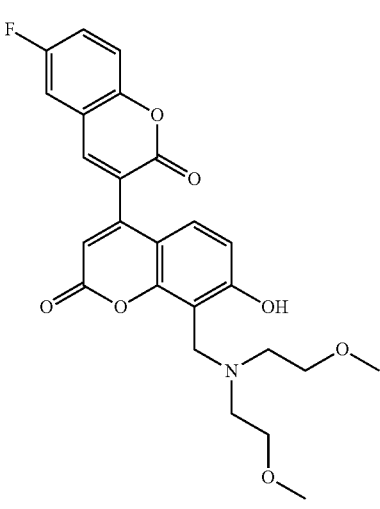
RT-0029
MW: 469.46
or a pharmaceutically acceptable salt, solvate, or ester derivative thereof as an active ingredient.
The compounds shown above are novel compounds that have been synthesized by the present inventors. These compounds suppress cell division in experiments using cultured cells and as such, can be used as anticancer agents.

In the anticancer agent of the present invention, the targeted cancer is a cancer expressing at TACC3, particularly, colon cancer, ovary cancer, uterine cancer, breast cancer, esophagus cancer, lymphoma, glioma, prostate cancer, kidney cancer, or melanoma.

The compound of the present invention functions via TACC3 or a TACC3-TOGp complex and therefore acts on tumor cells expressing TACC3. Particularly, colon cancer, ovary cancer, uterine cancer, breast cancer, esophagus cancer, or lymphoma often overexpresses TACC3. An anticancer agent comprising the compound of the present invention as an active ingredient is therefore confirmed to effectively act on these cancer types.

Furthermore, the compound of the present invention exhibits a high cell division inhibitory or arresting effect on ovary cancer, colon cancer, glioma, prostate cancer, kidney cancer, or melanoma. An anticancer agent comprising the compound of the present invention as an active ingredient is therefore confirmed to effectively act on these cancer types.

In addition, mouse experiments on lymphoma have revealed an apoptosis-induced tumor regression effect through the inhibition of TACC3 and also revealed the cell death-inducing effect of the compound of the present invention. An anticancer agent comprising the compound of the present invention as an active ingredient is therefore confirmed to effectively act on these cancer types.

The anticancer agent composition of the present invention is a composition for oral administration.

Since the compound of the present invention has been found effective through oral administration in experiments using mice, the composition can be provided as an oral formulation. Such oral administration eliminates the need of injection by physicians, and patients can continue treatment even at home without visiting hospitals. In addition, such oral formulations can be relatively easily used in combination with other agents and as such, can be expected to have a wide range of applications and effects.

The present invention also provides a method for producing an anticancer agent composition, comprising mixing the compound of the present invention or a pharmaceutically acceptable salt, solvate, or ester derivative thereof with a pharmaceutically acceptable excipient.

The compound disclosed in the present invention can be mixed as an active ingredient with an excipient to thereby produce an anticancer agent composition selectively acting on tumor cells expressing TACC3.

Advantageous Effects of Invention

The present invention can provide a drug, particularly, an anticancer agent, targeting at TACC3. Also, the compound disclosed in the present invention selectively inhibits the functions of spindles and mitotic apparatuses via a TACC3-TOGp complex and therefore selectively targets only actively dividing tumor cells expressing TACC3. The compound of the present invention is orally administrable and as such, can be expected to be widely applied clinically.

BRIEF DESCRIPTION OF THE DRAWINGS

FIG. 5A is a diagram showing the results of analysis using SKOV-3 cells. FIG. 5B is a diagram showing the results of analysis using OVCAR-3 cells.

FIG. 10A shows results of analyzing the growth inhibitory effects of SPL-A. FIG. 10B shows results of other anticancer agents.

FIG. 11A shows a growth inhibitory effect by the combined use of SPL-B and paclitaxel. FIG. 11B shows effect by the single use of SPL-B.

DESCRIPTION OF THE EMBODIMENTS

Figure 1:
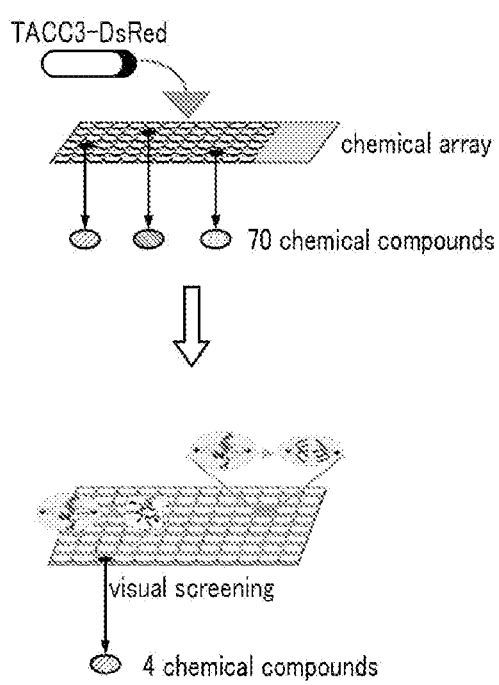
FIG. 1 Schematic diagram of a method for screening for a compound binding to TACC3 using a chemical array.

The present invention provides a compound targeting at TACC3. The compound targeting at TACC3 means a compound that binds to the TACC3 protein and thereby inhibits its effects.

TACC3 is a protein member of the TACC family. The nucleotide sequence of a gene encoding TACC3 and the amino acid sequence thereof are disclosed on databases under, for example, GenBank Accession No. NM_006342.1 and UniProt Accession No. Q9Y6A5.

The disease to which the inhibition of functions of the TACC3 gene or the TACC3 protein is advantageous is not limited and is preferably a tumor. In the present invention, the terms "cancer" and "tumor" are used interchangeably.

TACC3 is highly expressed in tumor cells compared with corresponding non-tumor cells. The expression means gene and/or protein expression, unless otherwise specified.

The tumor is not limited and is selected from the group consisting of sarcoma, leukemia, biliary tract cancer, breast cancer, uterine cancer, colorectal cancer, throat cancer, esophagus cancer, stomach cancer, colon cancer, tonsillar cancer, tongue cancer, neck cancer, lymphoma, lung cancer, thyroid gland cancer, ovary cancer, kidney cancer, pancreas cancer, brain tumor, myeloma, glioma, melanoma, liver cancer, prostate cancer, and urinary bladder cancer, preferably ovary cancer, breast cancer, uterine cancer, esophagus cancer, stomach cancer, colon cancer, pancreas cancer, prostate cancer, lymphoma, myeloma, glioma, kidney cancer, and melanoma, particularly preferably colon cancer, ovary cancer, uterine cancer, breast cancer, esophagus cancer, lymphoma, glioma, prostate cancer, kidney cancer, and melanoma.

The drug of the present invention is a drug for the treatment of actively dividing cells or tumor cells expressing TACC3. The treatment means the inhibition of abnormal cell growth of TACC3-expressing cells, or the induction of cell death, preferably tumor cells, highly expressing TACC3, thereby causing the delay or inhibition of tumor growth and the regression of a disease or a disorder, particularly, a tumor in a subject.

Examples of the pharmaceutically acceptable salt of the compound or the drug of the present invention include salts with inorganic and organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, and p-toluenesulfonic acid. Other examples thereof include base salts such as sodium hydroxide, potassium hydroxide, potassium carbonate, sodium bicarbonate, ammonia, amine salts, and trialkylamine salts.

Examples of the pharmaceutically acceptable ester derivative include ester compounds with alcohols or carboxylic acids each having 1 to 10 carbon atoms, preferably methyl alcohol, ethyl alcohol, acetic acid, or propionic acid.

Preferred examples of the pharmaceutically acceptable solvate include solvates with water.

Such a salt, ester derivative, and solvate can be formed by those skilled in the art using standard techniques.

The drug of the present invention may be orally administered in the dosage form of, for example, tablets, coated tablets, sugar-coated tablets, hard or soft gelatin capsules, solutions, emulsions, or suspensions. Alternatively, the drug of the present invention may be intrarectally administered by use of, for example, a suppository. Alternatively, the drug of the present invention may be administered locally or percutaneously by use of, for example, an ointment, a cream, a gel, or a solution. Also, the drug of the present invention may be administered parenterally, for example, intravenously, intramuscularly, subcutaneously, intraspinally, or intracutaneously by injection. Intravenous, intramuscular, or oral administration is preferred. Oral administration is most preferred. The drug of the present invention can be administered once or several times a day, though the number of doses is not limited thereto.

The drug of the present invention may be mixed with a pharmaceutically inert inorganic or organic excipient. Examples of appropriate excipients for tablets, sugar-coated tablets, or hard gelatin capsules include lactose, corn starch and derivatives thereof, talc, and stearic acid and salts thereof. Examples of appropriate excipients for use in soft gelatin capsules include plant oils, waxes, fats, and semisolid or liquid polyols. Examples of excipients for preparing solutions and syrups include water, polyols, saccharose, invert sugars, and glucose. Examples of excipients for injections include water, alcohols, polyols, glycerin, and plant oils. Examples of excipients for suppositories and local or percutaneous application include natural or hydrogenated oils, waxes, fats, and semisolid or liquid polyols. The drug of the present invention may further contain an antiseptic, a solubilizer, a stabilizer, a wetting agent, an emulsifier, a sweetener, a colorant, a flavoring agent, a salt changing osmotic pressure, a buffer, a coating agent, or an antioxidant, etc. The drug of the present invention may further contain an additional therapeutically useful agent.

The effective amount or dose of the compound of the present invention is not particularly limited and can be appropriately selected according to method of administration, age, body weight, and symptoms.

The subject to be treated using the drug of the present invention is a mammal. The mammal can be any mammal such as mice, rats, rabbits, guinea pigs, dogs, cats, cattle, horses, goats, sheep, monkeys, and humans. The mammal is preferably a companion animal such as a dog or a cat, or a human, more preferably a human.

Hereinafter, the present invention will be described in detail with reference to Examples. However, the present invention is not intended to be limited by these Examples.

Example 1

Screening for Compound Binding to TACC3-DsRed Fusion Protein

The present inventors screened for compounds targeting at TACC3 using a chemical array (FIG. 1).

According to the protcol of Miyazaki et al. (Non Patent Literature 13), a cell lysate containing a TACC3-DsRed fusion protein was contacted with the chemical array to screen for a compound binding to the TACC3-DsRed fusion protein (FIG. 1, upper diagram).

The cell lysate containing a TACC3-DsRed fusion protein is prepared as follows.

Human TACC3 cDNA was cloned into pDsRed-Express-N1 (Registered Trade Mark) (manufactured by Clontech Laboratories, Inc.), which was then transferred to HEK293T cells. Forty eight hours after transfection, the cells were collected. The obtained cells were sonicated in PBS and centrifuged for removal of insoluble substances to obtain a cell lysate. The cell lysate was confirmed the presence of the TACC3-DsRed fusion protein using anti-TACC3 and anti-DsRed antibodies.

The cell lysate containing a TACC3-DsRed fusion protein was contacted with the chemical array. After washing, the TACC3-DsRed fusion protein bound with a compound immobilized on the chemical array was detected. The detection of the TACC3-DsRed fusion protein with a compound was carried out by the excitation of a chemical array slide with a wavelength of 532 nm and the detection of fluorescence at 575 nm.

As a result of screening 6800 compounds, 70 compounds were bound with the TACC3-DsRed fusion protein. These 70 compounds recognized to bind to the TACC3-DsRed fusion protein were each added into a culture medium of cultured cells. Compounds inducing abnormal cell division were selected by microscopic observation. As a result, 4 compounds were screened for as compounds inhibiting cell division (FIG. 1, lower diagram, visual screening).

Four compounds represented by the formulas (II) to (V) given below are compounds that bound to the TACC3-DsRed fusion protein and induced abnormal cell division. These compounds (II) to (V) immobilized on the chemical array were registered in the Riken natural products depository bank "RIKEN NPDepo" (http://npd.riken.jp/npd/) under NPD3574, NPD2568, NPD4089, and NPD2448 and are available from the bank.

[Formula 2]

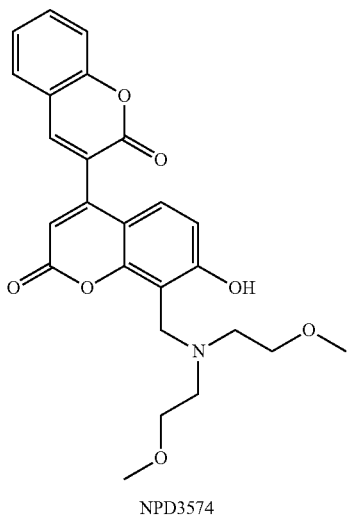

NPD3574

[Formula 3]

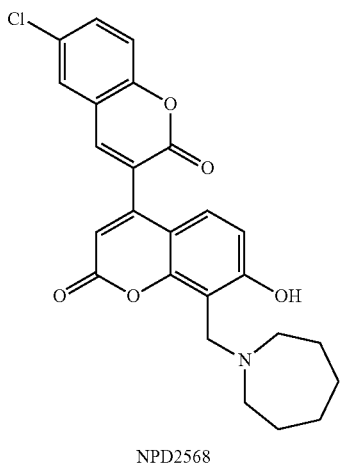

NPD2568

[Formula 4]

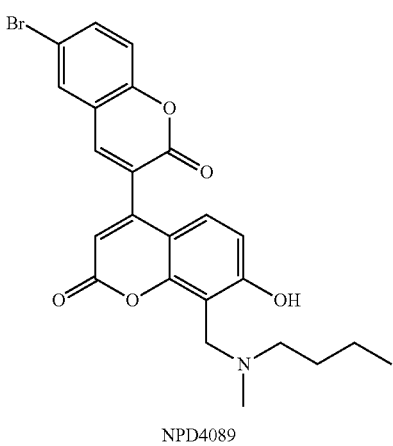

NPD4089

[Formula 5]

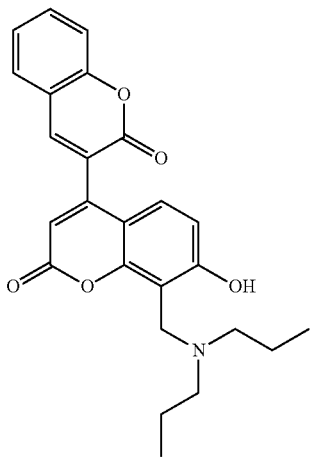

NPD2448

The 4 compounds NPD3574, NPD2568, NPD4089, and NPD2448 obtained by screening using the chemical array each have a dicoumarin structure represented by the formula (I) given below wherein an OH group is located at position $C_7$. Thus, the structure of the formula (I) is important for binding to TACC3.

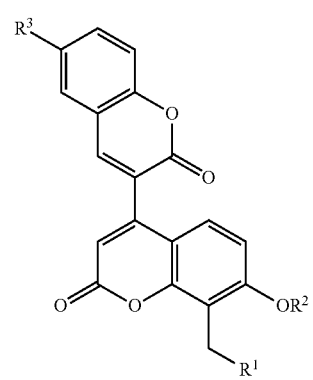

Example 2

Mitotic Arrest Induced by NPD Compounds

The 4 NPD compounds selected by screening using the chemical array were analyzed for their activity against cell division using synchronized culture.

The 4 compounds each have a dicoumarin structure having an OH group at position $C_7$, suggesting the importance of this OH group at position $C_7$. Thus, $C_7$—O-propylated NPD3574 was synthesized by propylation at position $C_7$ and analyzed, together with the 4 NPD compounds, for its influence on cell division of cultured cells.

Hereinafter, analysis methods will be described in detail.

(1) Preparation of EGFP-α-Tubulin-Expressing Cell

The EGFP-α-tubulin-expressing cells used in the assay will be described. In order to observe mitosis under a fluorescence microscope, cells expressing EGFP-α-tubulin (fusion protein of a fluorescent protein, EGFP, and α-tubulin) were prepared. A system observable under a fluorescence microscope without cell fixation was prepared.

Ovary cancer cells SKOV-3 were cultured in an RPM11640 medium supplemented with 5% fetal bovine serum. Stable cells expressing EGFP-α-tubulin were transduced by lentiviral transduction using pLenti4/V5-DEST Vectors (Registered Trade Mark) (manufactured by Invitrogen Corp.) and selected by the FACS sorting of infected cells using Zeocin (Registered Trade Mark) and subsequent FACSAria (Registered Trade Mark) (Becton, Dickinson and Company).

(2) Analysis of Mitotic Arrest by NPD Compound

The compounds NPD2448, NPD2568, NPD3574, NPD4089, and $C_7$—O-propylated NPD3574 were each added at varying concentrations to the culture medium of SKOV-3 cells expressing EGFP-α-tubulin and analyzed for their effect on cell division.

The SKOV-3 cells expressing EGFP-α-tubulin were synchronized by thymidine block to analyze the effect on cell division of each compound. As shown in the upper part of FIG. 2, each compound was added to the culture medium after the 1st thymidine block. After synchronization by the second thymidine block, images were taken every 2 minutes for 3 days using Leica AF6000 and ×20/0.5 Plan Fluotar objective lens in a phenol red-free RPM11640 medium supplemented with 5% fetal bovine serum. These time-lapse images were analyzed using ImageJ 1.42a software, and the time of mitotic arrest was determined by visual judgment. The duration of mitosis was manually determined from the image sequences of at least 50 cells.

(3) Results

Figure 2:
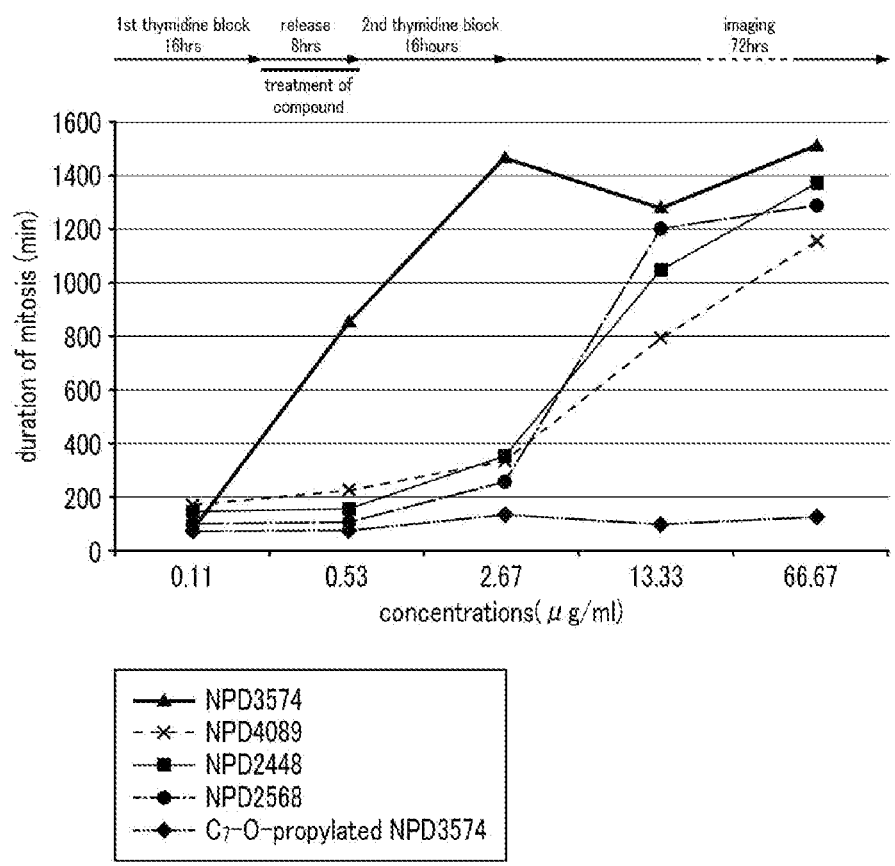
FIG. 2 Diagram showing a dose-dependent mitotic arrest by an NPD compound.

As shown in FIG. 2, the 4 compounds obtained by screening induced mitotic arrest in a concentration-dependent manner. The concentrations represent final concentrations. Dose-dependent ($EC_{50}$=0.3 to 8.0 μg/ml) mitotic arrest was observed for all of the 4 compounds. By contrast, $C_7$—O-propylated NPD3574 synthesized by propylation at position $C_7$ did not arrested mitosis.

Since $C_7$—O-propylated NPD3574 having the structure of the formula (I) but propylated at position $C_7$ lost mitotic arrest activity, the OH group at position $C_7$ is important for activity. In light of the structures of the 4 compounds obtained by screening, the N,N-disubstituted aminomethyl group at position $C_8$ was presumed to also serve as a principal determinant.

Example 3

Synthesis of Novel Compound

As mentioned above, the compounds represented by the general formula (I) having an OH group at position $C_7$ and a N,N-disubstituted aminomethyl group at position $C_8$, and having TACC3 binding activity were confirmed to have inhibitory activity of cell division. Thus, in order to obtain novel compounds having TACC3 binding activity and inhibitory activity of cell division, compounds having the basic structure of the formula (I) were synthesized.

The following 29 compounds were synthesized:

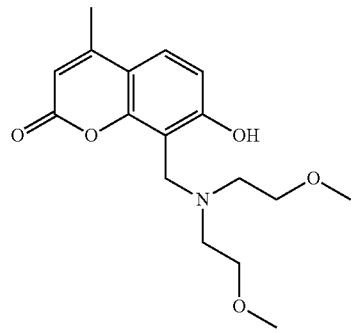

MW: 321.37

RT-001

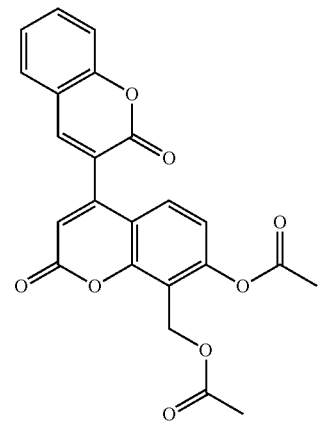

MW: 420.37

RT-002

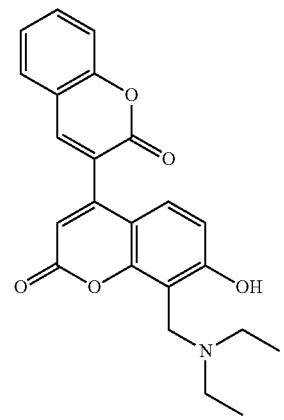

MW: 391.42

RT-003

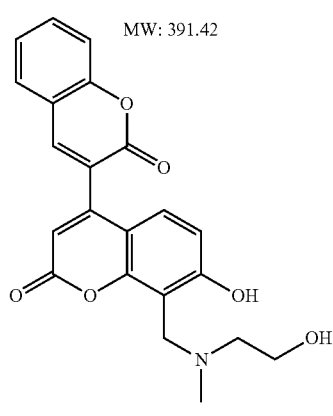

MW: 393.39

RT-004

RT-005
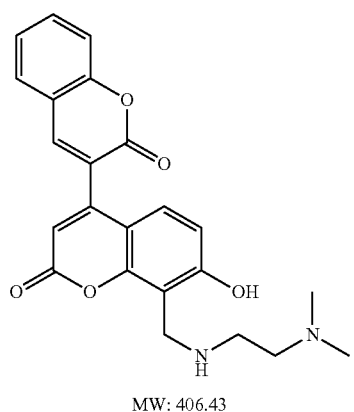
MW: 406.43
RT-006
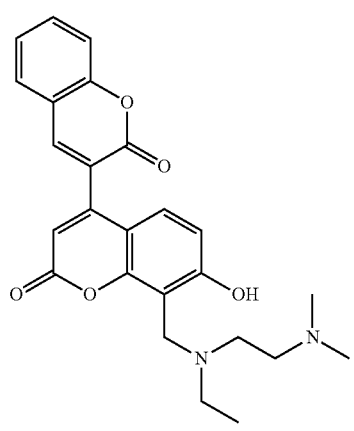
MW: 434.48
RT-007
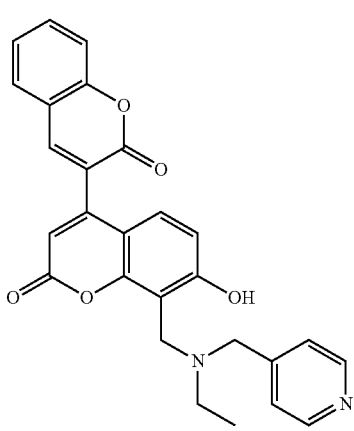
MW: 454.47
RT-008
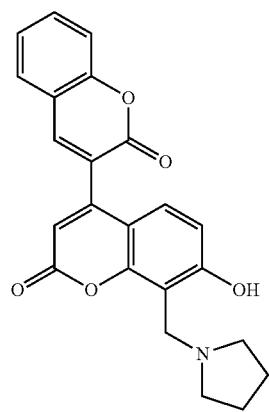
MW: 389.40
RT-009
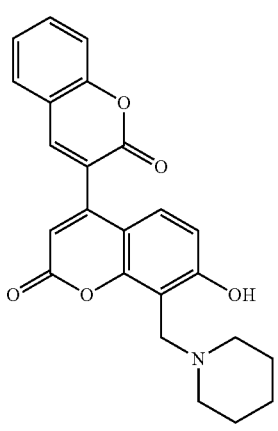
MW: 403.43
RT-010
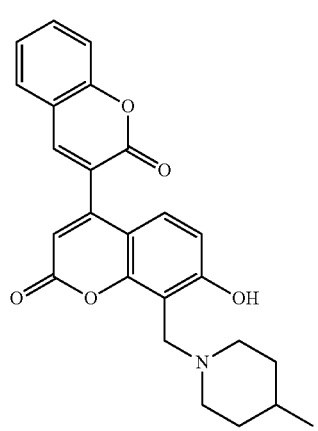
MW: 417.45

-continued
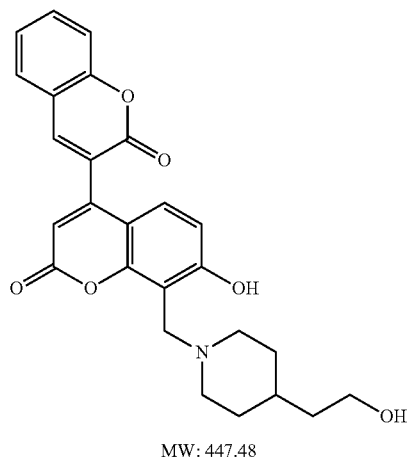
RT-011
MW: 447.48
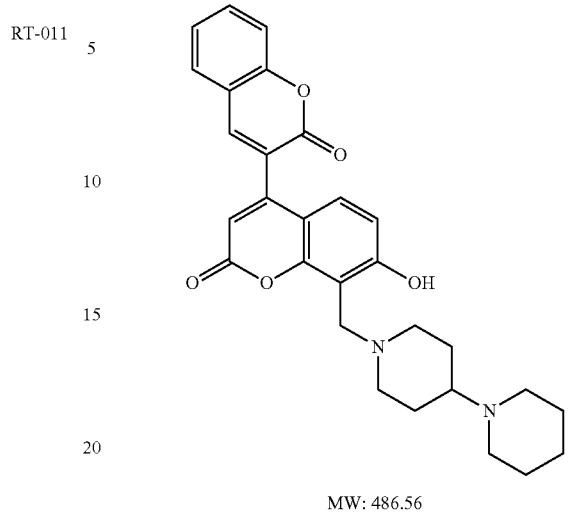
RT-014
MW: 486.56
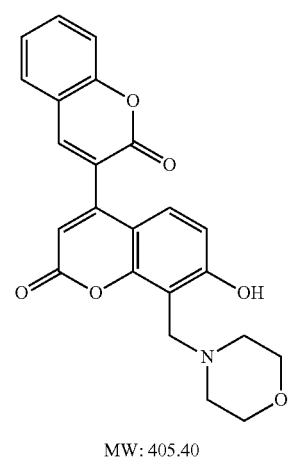
RT-012
MW: 405.40
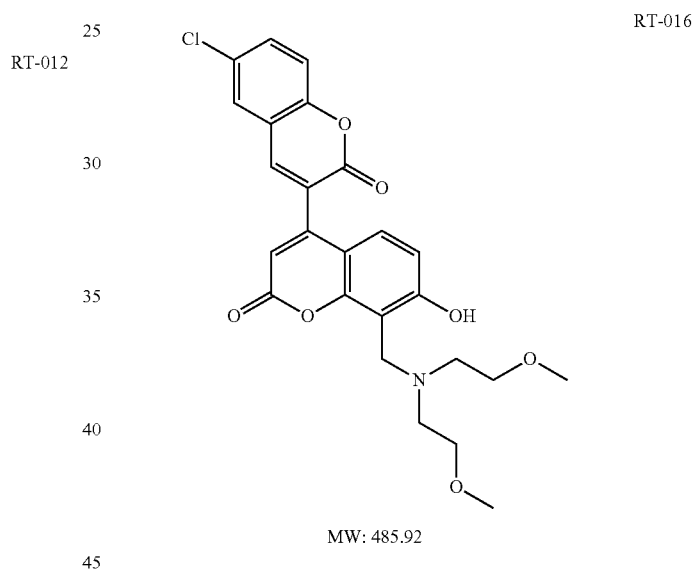
RT-016
MW: 485.92
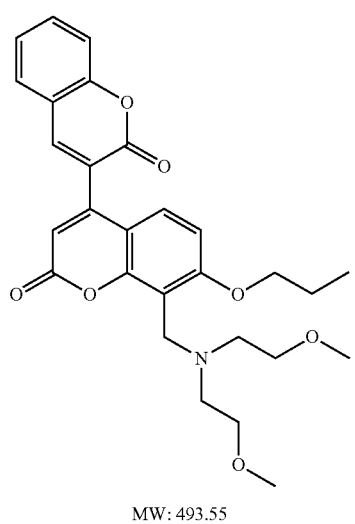
RT-013
MW: 493.55
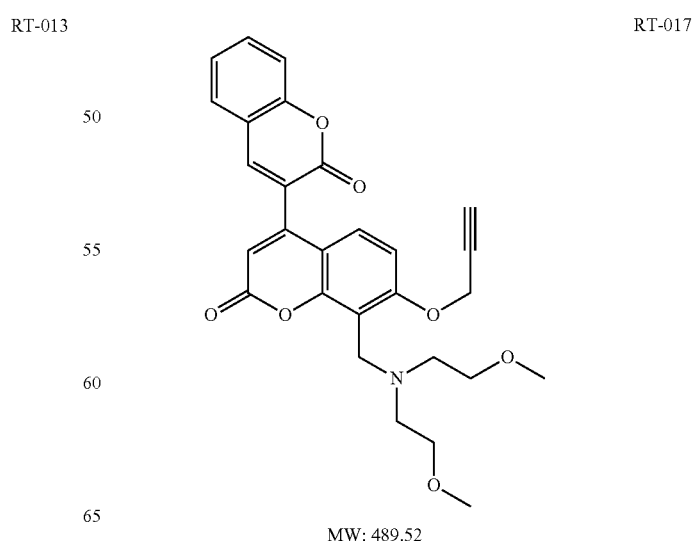
RT-017
MW: 489.52

RT-018
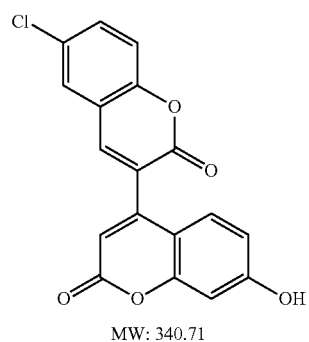
MW: 340.71
RT-019
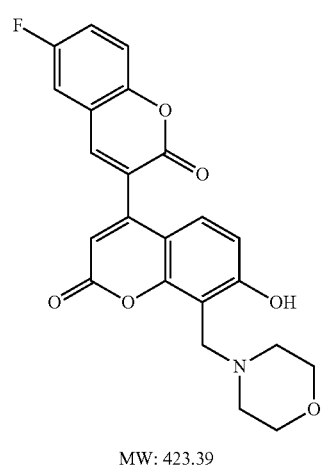
MW: 423.39
RT-020
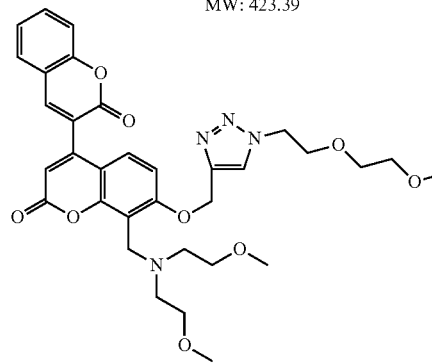
MW: 763.83
RT-021
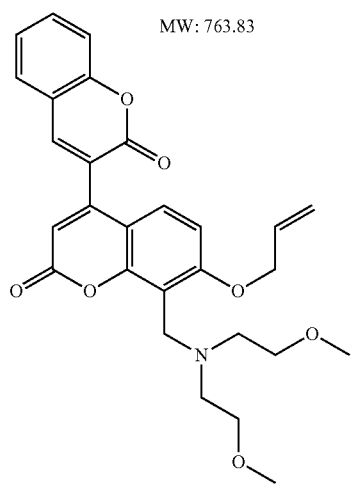
MW: 491.53
RT-022
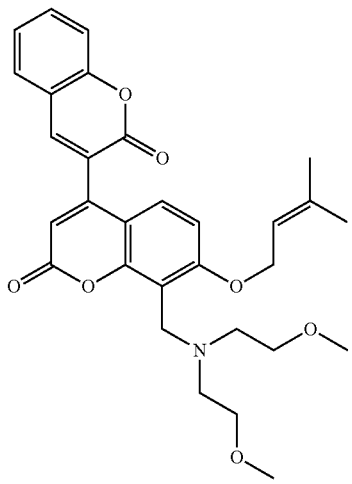
MW: 519.59
RT-023
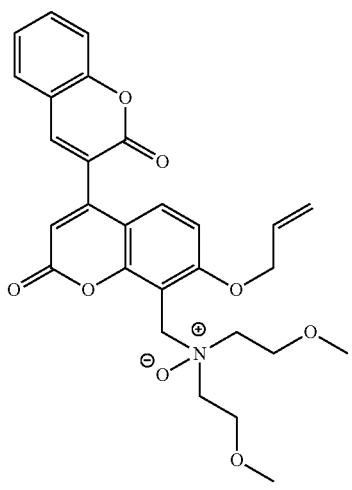
MW: 507.53
RT-024
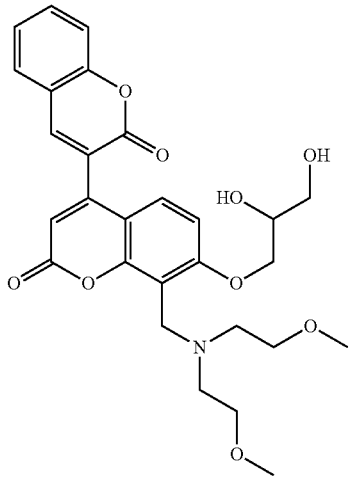
MW: 525.55

RT-025

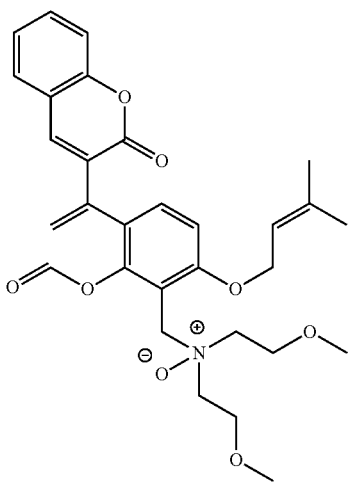

MW: 535.58

RT-026

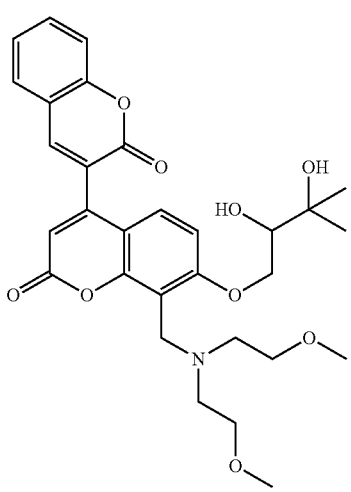

MW: 553.60

RT-027

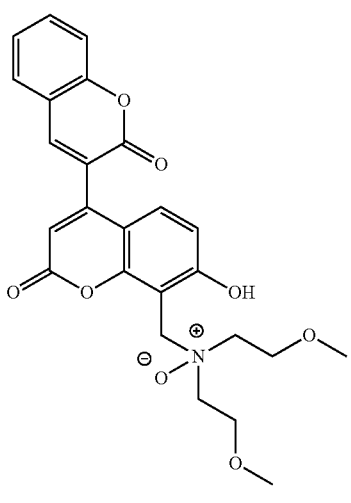

MW: 467.47

RT-028

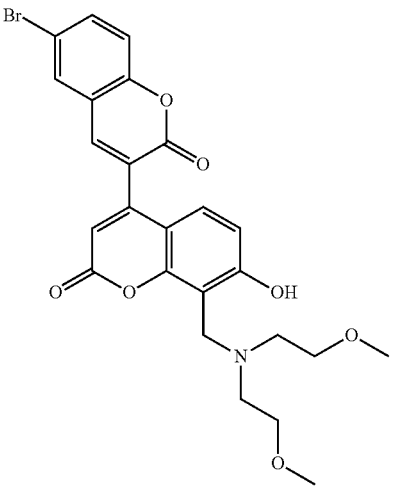

MW: 530.36

RT-029

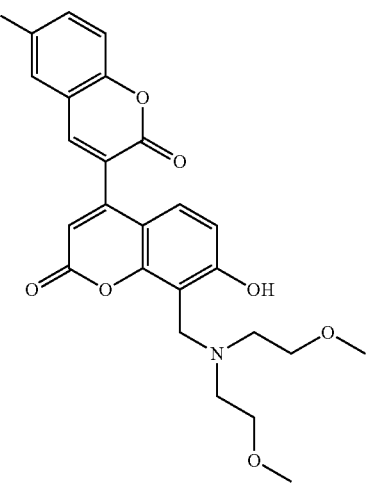

MW: 469.46

RT-030

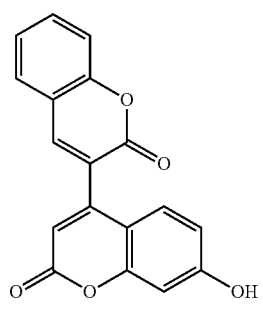

MW: 306.27

Hereinafter, synthesis methods will be described. Synthesis methods will be described in detail for two typical compounds RT-007 and RT-011 which are synthesized using dicoumarin as a starting material and two compounds RT-002 and RT-027 which are synthesized using the compound of the formula (II) (NPD3574) as a starting material. Other compounds can also be synthesized with the above-mentioned compounds or the like as starting materials.

(1) Example 3-1

Synthesis of RT-007

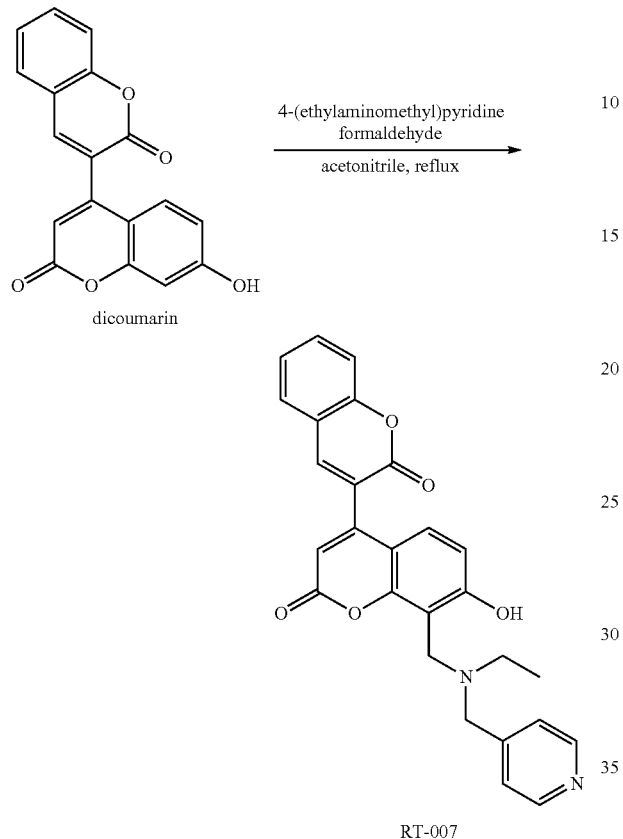

The method for synthesizing the starting material dicoumarin follows the procedure of Dubovic et al. (Non Patent Literature 14).

A 37% aqueous formaldehyde solution (458 μl, 6.21 mmol) and 4-(ethylaminomethyl)pyridine (267 mg, 1.96 mmol) were added to a stirring solution of dicoumarin (100 mg, 0.327 mmol) in acetonitrile (15 ml), and the mixture was heated for 24 hours under reflux. The reaction solution was cooled to room temperature and diluted with $CHCl_3$. The organic layer was washed with water and saturated saline in this order and then dried over $Na_2SO_4$, and the solvent was distilled off. The residue was crudely separated by preparative TLC ($CHCl_3$:MeOH=20:1) and then further purified by preparative TLC ($CHCl_3$:MeOH=50:1) to obtain RT-007 (yellow solid, 73.7 mg, yield: 49%).

The NMR data of the compound RT-007 obtained by synthesis is as follows:

$^1$H NMR (500 MHz, $CDCl_3$) δ=1.21 (t, J=6.9 Hz, 3H), 2.69 (q, J=6.9 Hz, 2H), 3.73 (brs, 2H), 4.16 (s, 2H), 6.28 (s, 1H), 6.74 (d, J=9.2 Hz, 1H), 7.20 (d, J=9.2 Hz, 1H), 7.28 (dd, J=4.6, 1.7 Hz, 2H), 7.38 (ddd, J=7.4, 7.4, 1.1 Hz, 1H), 7.43 (brd, J=8.6 Hz, 1H), 7.61 (dd, J=7.4, 1.7 Hz, 1H), 7.66 (ddd, J=8.6, 7.4, 1.7 Hz, 1H), 7.87 (s, 1H), 8.60 (dd, J=4.6, 1.7 Hz, 2H).

$^{13}$C NMR (125 MHz, $CDCl_3$) δ=11.0, 47.6, 49.9, 57.0, 108.4, 110.5, 112.3, 113.8, 116.9, 118.3, 124.0, 124.1, 125.1, 126.5, 128.5, 133.1, 143.3, 145.6, 150.1, 150.2, 152.9, 154.2, 159.0, 160.6, 162.8.

HRMS-FAB: m/z $[M+H]^+$ calcd for $C_{27}H_{23}N_2O_5$: 455.1607. found: 455.1589. $[M+Na]^+$ calcd for $C_{27}H_{22}N_2NaO_5$: 477.1426. found: 477.1423.

(2) Example 3-2

Synthesis of RT-011

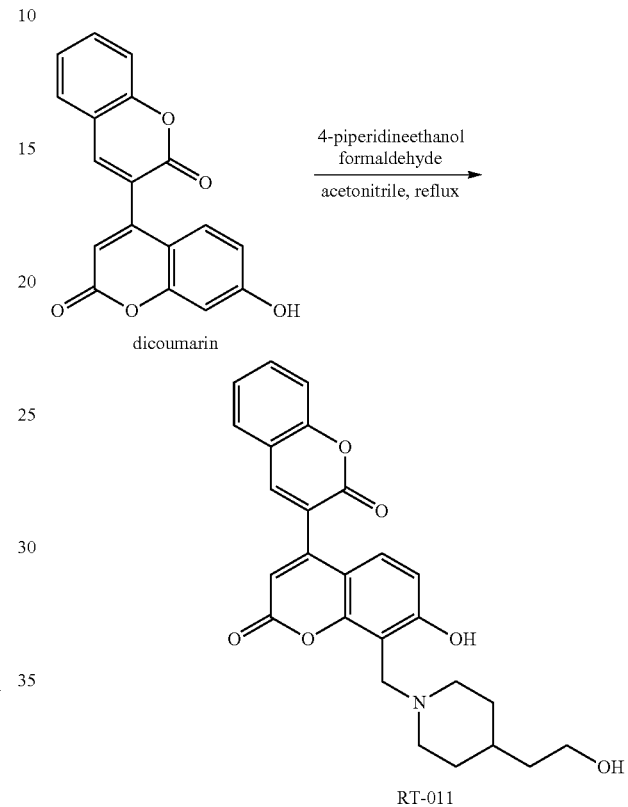

A 37% aqueous formaldehyde solution (17.7 μl, 240 mol) and 4-piperidine ethanol (9.7 mg, 75.0 mol) were added at room temperature (approximately 23° C.) to a solution of dicoumarin (9.2 mg, 30.0 μmol) in acetonitrile (3.5 ml). This stirring solution of the reaction mixture was heated for 24 hours under reflux. The mixed solution was cooled to room temperature and diluted with $CHCl_3$. The organic layer was washed with water and saturated saline in this order and then dried over $Na_2SO_4$, and the solvent was distilled off. The obtained residue was crudely separated by preparative TLC ($CHCl_3$:MeOH=20:1) and then further purified by preparative TLC ($CHCl_3$:MeOH=10:1) to obtain RT-011 (yellow oily product, 10.2 mg, yield: 76%) as an yellow oil.

The NMR data of the compound RT-011 obtained by synthesis is as follows:

$^1$H NMR (500 MHz, $CDCl_3$) δ=1.32 (m, 2H), 1.53 (m, 3H), 1.79 (brd, J=12.6 Hz, 2H), 2.24 (brs, 2H), 3.03 (brs, 2H), 3.70 (t, J=6.9 Hz, 2H), 4.04 (s, 2H), 6.22 (s, 1H), 6.67 (d, J=9.2 Hz, 1H), 7.15 (d, J=9.2 Hz, 1H), 7.36 (brdd, J=7.4, 7.4 Hz, 1H), 7.42 (brd, J=8.6 Hz, 1H), 7.57 (dd, J=7.4, 1.7 Hz, 1H), 7.63 (ddd, J=8.6, 7.4, 1.7 Hz, 1H), 7.82 (s, 1H).

$^{13}$C NMR (125 MHz, $CDCl_3$) δ=32.0, 39.0, 53.3, 54.3, 60.3, 108.1, 110.2, 114.0, 117.0, 118.4, 124.3, 125.0, 126.2, 128.5, 133.0, 143.1, 150.1, 152.9, 154.3, 159.0, 160.7, 168.8. HRMS-FAB: m/z $[M+H]^+$ calcd for $C_{26}H_{26}NO_6$: 448.1760. found: 448.1764.

(3) Example 3-3

RT-002 and RT-027 were synthesized with NPD3574 as a starting material as follows:

Synthesis of RT-002

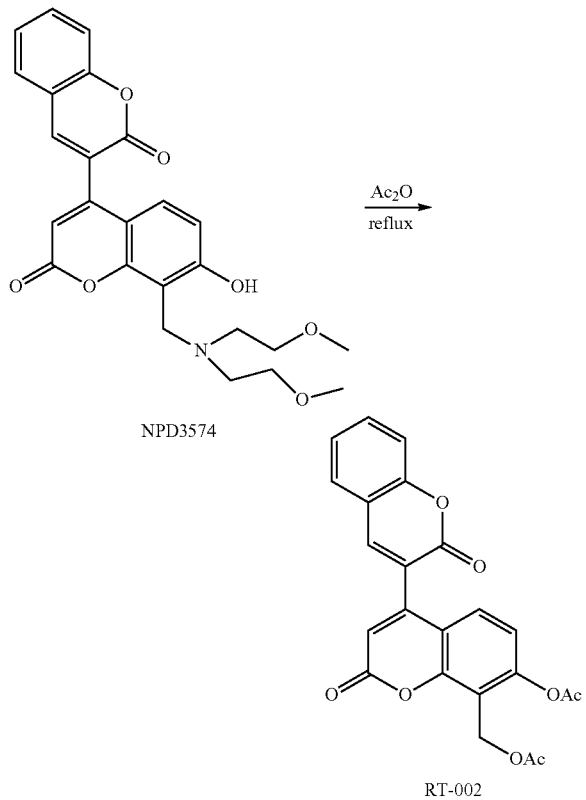

An acetic anhydride (4 mL) solution of NPD3574 (6.6 mg, 15 mol) was stirred for 10 hours under heating to reflux. The reaction solution was brought back to room temperature, and acetic anhydride was then distilled off under reduced pressure. $CHCl_3$ was added to the residue. The organic layer was washed with $H_2O$ and saturated saline in this order and then dried over $Na_2SO_4$, and the solvent was distilled off. The residue was purified by preparative TLC ($CHCl_3$:MeOH=20:1) to obtain RT-002 (colorless crystal, 5.3 mg, 84%).

(4) Example 3-4

Synthesis of RT-027

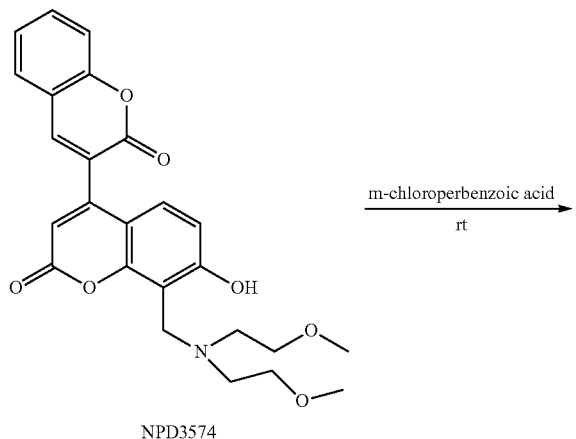

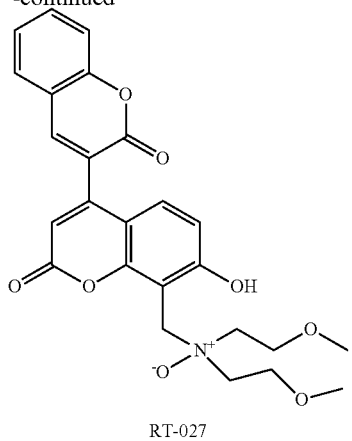

m-Chloroperbenzoic acid (77% purity, 3.0 mg, 13.3 mol) was added to a $CH_2Cl_2$ (5 mL) solution of NPD3574 (5.0 mg, 11.1 mol), and the mixture was stirred at room temperature for 4 hours. Then, the reaction solution was diluted with $CHCl_3$. The organic layer was washed with saturated aqueous solution of $Na_2CO_3$ and saturated saline in this order and then dried over $Na_2SO_4$, and the solvent was distilled off. The residue was purified by preparative TLC ($CHCl_3$:MeOH=10:1) to obtain RT-027 (yellow oily product, 3.9 mg, 75%).

Other compounds can also be synthesized in the same way as above by use of amines described in Table 1 below. Table 1 shows amines used in the synthesis of compounds having inhibitory activity of cell growth as shown in Table 2 below among 30 synthesized compounds.

TABLE 1

| Compound | $R^1$ | Amine |
|---|---|---|
| RT-002 | OAc | See Example 3-3 |
| RT-003 | $NEt_2$ | Diethylamine |
| RT-004 | $NMe(CH_2CH_2OH)$ | N-methylethanolamine |
| RT-005 | $NH(CH_2CH_2NMe_2)$ | N,N-dimethylethylenediamine |
| RT-006 | $NEt(CH_2CH_2NMe_2)$ | N,N-dimethyl-N'-ethylethylenediamine |
| RT-007 | | 4-(ethylaminomethyl)pyridine |
| RT-008 | | Pyrrolidine |
| RT-009 | | Piperidine |
| RT-010 | | 4-pipecoline |
| RT-011 | | 4-piperidineethanol |

TABLE 1-continued

| Compound | R¹ | Amine |
|---|---|---|
| RT-012 | (morpholine ring structure) | Morpholine |
| RT-014 | (piperidinopiperidine structure) | 4-piperidinopiperidine |
| RT-016 | N(CH$_2$CH$_2$OMe)$_2$ | bis(2-methoxyethyl)amine |
| RT-019 | (morpholine ring structure) | Morpholine |
| RT-027 | N$^+$O$^-$(CH$_2$CH$_2$OMe)$_2$ | See Example 3-4 |
| RT-028 | N(CH$_2$CH$_2$OMe)$_2$ | bis(2-methoxyethyl)amine |
| RT-029 | N(CH$_2$CH$_2$OMe)$_2$ | bis(2-methoxyethyl)amine |

Example 4

Assay on mitotic arrest (EC$_{50}$=50% arrest rate) of SKOV-3 and cell death (IC$_{50}$=50% survival rate) of lymphoma The 29 compounds synthesized in Example 3 and NPD3574 used as a starting material in the synthesis of RT-002 and RT-027 were analyzed for their inhibitory activity of cell growth.

(1) Effect on Mitotic Arrest (EC$_{50}$=50% Arrest Rate)

The mitotic arrest (EC$_{50}$=50% arrest rate) was tested by the microscopic analysis of individual single cells.

EGFP-α-tubulin-expressing SKOV-3 cells synchronized by double thymidine block in the same way as in Example 2 were treated with each synthesized compound and subjected to time-lapse photography for 3 days. At least 50 cells were observed. The time of arrest of each cell was calculated, and EC$_{50}$ was determined therefrom.

(2) Calculation of Cell Death (IC$_{50}$=50% Survival Rate)

The synthesized compounds were analyzed for their activity against cell death induction using a mouse lymphoma cell line (see Non Patent Literature 12), which was a cell line derived from thymic lymphoma developed in p53KO mouse.

The number of the lymphoma cells was adjusted to 1.2×10$^5$ cells/ml. The cells were inoculated at a concentration of 50 µl/well to a 96-well culture dish. A medium containing each RT compound as the novel compound of the present invention at twice the concentration of 50 µl was further added thereto (final concentration: 0.021 to 13.3 µg/ml). Three days after cultivation, the survival rate was calculated using WST-1 reagent (manufactured by F. Hoffmann-La Roche, Ltd.).

(3) Results

Table 2 below describes compounds in order of the strength of inhibitory effect on cell growth. The compounds RT-007, RT-016, RT-019, RT-029, RT-011, RT-003, RT-010, RT-006, RT-012, RT-009, RT-008, RT-027, RT-028, RT-014, RT-004, RT-002, RT-005, and NPD3574 were confirmed to have remarkable inhibitory effects on cell growth.

Particularly, RT-007 was found effective at concentrations as very low as EC$_{50}$ of 0.05 µg/ml in the analysis using SKOV-3 and IC$_{50}$ of 0.02 µg/ml in the analysis using lymphoma.

TABLE 2

| Compound | SKOV3 EC$_{50}$ (µg/ml) | lymphoma IC$_{50}$ (µg/ml) | Remarks |
|---|---|---|---|
| RT-007 | 0.05 | 0.02 | SPL-B |
| RT-016 | 0.15 | 0.20 | |
| RT-019 | 0.16 | 0.12 | |
| RT-029 | 0.17 | 0.21 | |
| RT-011 | 0.79 | 2.15 | SPL-A |
| RT-003 | 0.85 | 5.08 | |
| NPD3574 | 0.85 | 1.26 | |
| RT-010 | 0.94 | 1.64 | |
| RT-006 | 1.15 | 3.30 | |
| RT-012 | 1.39 | 2.05 | |
| RT-009 | 2.68 | 10.13 | |
| RT-008 | 2.67 | 9.77 | |
| RT-027 | 4.96 | 8.74 | |
| RT-028 | 6.56 | 3.28 | |
| RT-014 | 8.76 | 8.25 | |
| RT-004 | 8.49 | 13.3< | |
| RT-002 | 13.3< | 8.30 | Cytotoxic. At 66.7 µg/ml, mitosis did not start. |
| RT-005 | 13.3< | 5.37 | Cytotoxic. At 66.7 µg/ml, mitosis did not start. |
| RT-001 | 66.7< | | |
| RT-013 | 66.7< | | |
| RT-017 | 66.7< | | Insoluble |
| RT-018 | 66.7< | | Poorly soluble in DMSO |
| RT-020 | 66.7< | | Insoluble |
| RT-021 | 66.7< | | Insoluble |
| RT-022 | 66.7< | | Insoluble. At 66.7 µg/ml, mitosis did not start. |
| RT-023 | 66.7< | | |
| RT-024 | 66.7< | | |
| RT-025 | 66.7< | | |
| RT-026 | 66.7< | | |
| RT-030 | 66.7< | | |

These results demonstrated that the compounds having the structure of the general formula (I) and having the following particular groups as R¹, R², and R³ have a cell growth inhibitory effect:

R¹ represents

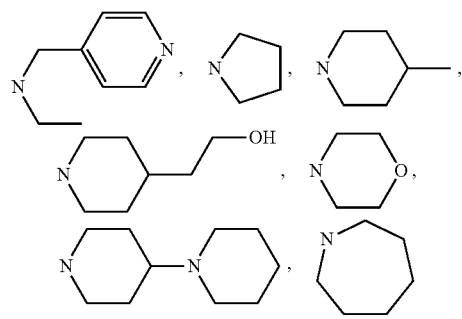

OAc, NEt$_2$, NMe(CH$_2$CH$_2$OH), NH(CH$_2$CH$_2$NMe$_2$), NEt(CH$_2$CH$_2$NMe$_2$), N(CH$_2$CH$_2$OMe)$_2$, N$^+$O$^-$(CH$_2$CH$_2$OMe)$_2$, NMe(CH$_2$)$_3$Me, or N(CH$_2$CH$_2$Me)$_2$; R² represents Ac or H; and R³ represents H, Cl, F, or Br.

Since these compounds exhibit a cell growth inhibitory effect, the compounds used in anticancer agents or the like can be expected to inhibit the growth of tumor cells. Thus, these compounds were analyzed in detail for inhibitory effects on their cell growth, particularly, their effects on cell division.

RT-011 and RT-007 having effects at distinctive concentrations were selected from 18 compounds determined to have superior effects as to mitotic arrest and cell death among the above-mentioned tested 30 novel compounds.

The selected compounds were designated as SPL-A and SPL-B, respectively, and analyzed in detail. The results will be described below.

Example 5

Effects of SPL-A and SPL-B on Cell Division

Of the observed 18 compounds that had a cell growth inhibitory effect on SKOV-3 and mouse lymphoma, SPL-A and SPL-B were analyzed for their dose-dependency of mitotic arrest in order to study the effects of these SPL compounds on cell division.

EGFP-α-tubulin-expressing SKOV-3 cells supplemented with each of SPL-A and SPL-B at varying concentrations were synchronized by double thymidine block in the same way as in Example 2. Analysis based on single cells was conducted by time-lapse photography. The duration of mitosis was measured from the image sequences of at least 50 cells.

Figure 3:
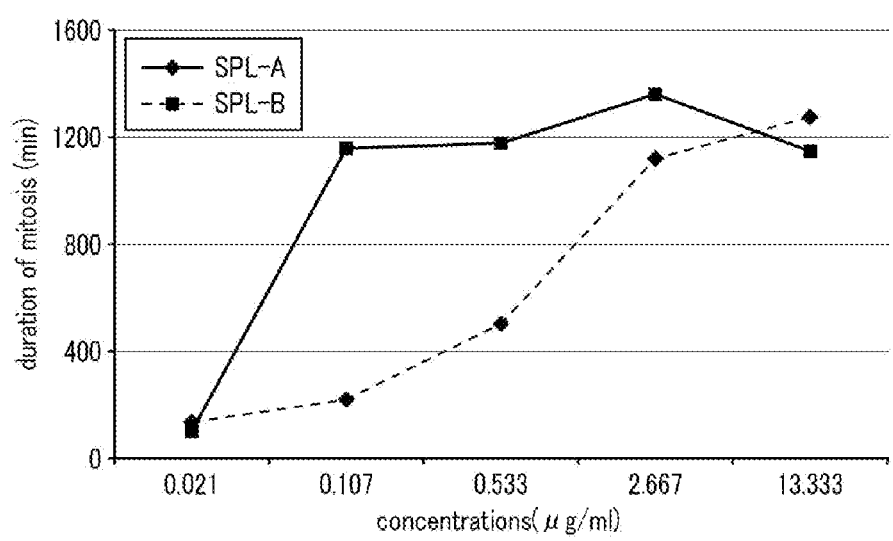
FIG. 3 Diagram showing a dose-dependent mitotic arrest by SPL (Spindlactone).

The concentrations in FIG. 3 represent final concentrations. SPL-A induced mitotic arrest at 2.667 µg/ml, whereas SPL-B induced mitotic arrest at 0.107 µg/ml. SPL-B was more highly active than SPL-A against mitotic arrest. These results are also consistent with the results of analysis of mitotic arrest and cell death shown in Table 2.

Example 6

Cell Fate Analysis by Treatment with SPLA and SPL-B

As shown in FIG. 3, SPL-A and SPL-B induce mitotic arrest in a concentration-dependent manner. Thus, analysis was made on at what period during the cell cycle mitotic arrest would occur.

(1) Cell Fate Determination by Time-Lapse Photography

The cells used were SKOV-3 cells and OVCAR-3 cells expressing EGFP-α-tubulin.

The OVCAR-3 cells expressing EGFP-α-tubulin were obtained using the same procedure as that for the SKOV-3 cells expressing EGFP-α-tubulin. The cells supplemented with each of SPLA and SPL-B were synchronized by double thymidine block in the same way as in Example 2. Images were obtained by time-lapse photography and analyzed. The cells of each line were treated with 13.3 µg/ml SPL-A or 2.7 µg/ml SPL-B. The cell fate was manually determined from the image sequence of at least 50 cells with the time point of nuclear envelope breakdown defined as 0.

(2) Results

Figure 4:
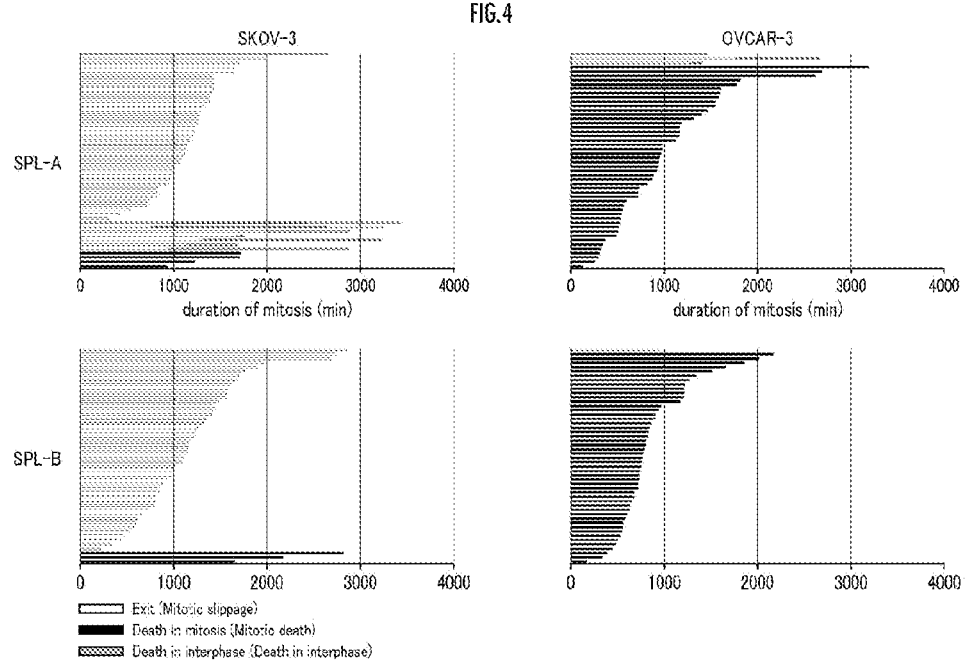
FIG. 4 Diagram showing results of analyzing cell fate using SPL-treated SKOV-3 cells and OVCAR-3 cells.

The analysis results are shown in FIG. 4. Although mitosis is arrested, and cell growth is inhibited in SKOV-3 and OVCAR-3, the time of arrest during the cell cycle differs between SKOV-3 and OVCAR-3.

Most of the SKOV-3 cells treated with SPL-A exhibit mitotic slippage. The mitotic slippage occurs by the sustention of cell cycle arrest at the cell division stage. Some cells underwent death in interphase after mitotic slippage, and mitotic death. Also, most of the SKOV-3 cells treated with SPL-B exhibited mitotic slippage, while mitotic death was observed in some cells.

On the other hand, most of the OVCAR-3 cells treated with SPL-A exhibited mitotic death, while death in interphase after mitotic slippage, and mitotic slippage were observed in some cells. Also, most of the OVCAR-3 cells treated with SPL-B exhibited mitotic death, while mitotic slippage was observed in some cells. After delayed mitotic arrest, both of the compounds induced mitotic arrest in SKOV-3 or induced mitotic death in OVCAR-3.

These results are consistent with results of an experiment on cell fate determination of SKOV-3 and OVCAR-3 by the suppression of TACC3 expression using shRNA. Specifically, the suppression of TACC3 expression using shRNA induces mitotic slippage (which occurs by the sustention of cell cycle arrest at the cell division stage) in SKOV-3 and mitotic death in OVCAR-3.

The results of analysis using SPL-A and SPL-B are very consistent with the results of the experiment on the suppression of TACC3 expression using shRNA, suggesting that SPL targets TACC3.

Example 7

Change in Abnormal Cell Division Depending on Concentration of SPL Compound

From the results mentioned above, SPL-A and SPL-B were confirmed to exhibit similar effects on the cell cycle of the same cells. Thus, SPL-A was added in a concentration-dependent manner, and cells containing spindles with abnormal morphology were analyzed using SKOV-3 cells and OVCAR-3 cells.

(1) Analysis of Abnormal Spindle Morphology in Cell Treated with SPL-A

SPL-A was added at each concentration to the SKOV-3 or OVCAR-3 cells. Twenty four hours after incubation, the cells were fixed and immunostained using antibodies against cell division-related substances such as α-tubulin described below. The percentage of spindle morphology was determined from at least 50 cells. The data was indicated by a mean of three independent experiments and SD.

The immunostaining was carried out by the following method: the cells were fixed in 3.7% PFA, methanol, or 10% TCA on a chamber slide, then permeabilized with 0.2% Triton-X100 in PBS, and incubated with primary antibodies. A monoclonal antibody (DM1A) against α-tubulin and monoclonal antibodies (DQ19 and GTU-88) against γ-tubulin were obtained from Sigma-Aldrich Corp. An anti-centrin 2 antibody (sc-27793) was purchased from Santa Cruz Biotechnology, Inc. Fluorescent labelled goat anti-mouse IgG (Cappel) and Cy3 labelled goat anti-rabbit IgG (Millipore) antibodies were used as secondary antibodies. DNA was detected using 4,6-diamidino-2-phenylindole (DAPI). Images were obtained using Leica DM6000B microscope equipped with ×100/1.40-0.70 PlanApo objective lens and Z-projections.

(2) Results

Figure 5:
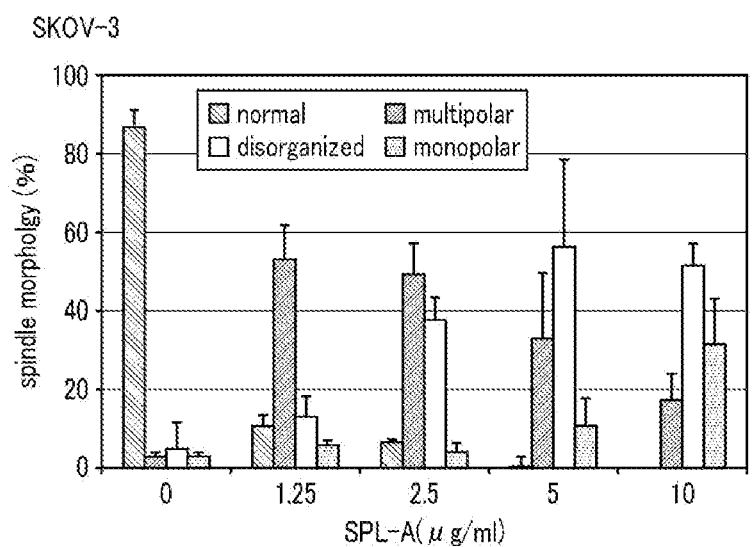
FIG. 5 Diagram showing the percentage of spindle morphology of cells containing abnormal spindles induced by SPL treatment.
Figure 5:
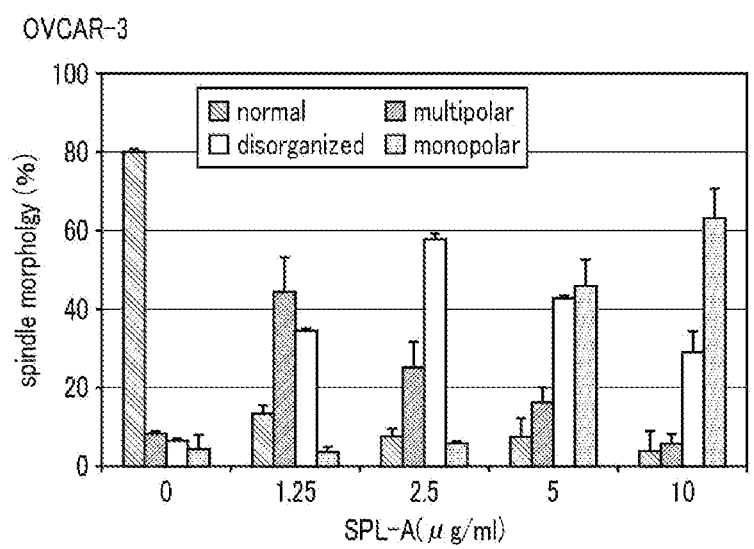

FIG. 5 shows the results of analyzing spindle morphology. The percentage of spindle morphology was indicated by the percentage (%) of normal, multipolar, disorganized, or monopolar spindles to the number of mitotic cells. The concentrations represent final concentrations. At each concentration, normal, multipolar, disorganized, and monopolar are shown from the left to the right. Normal means the state where spindles were arranged in a bipolar configuration (normal state). Disorganized, multipolar, or monopolar refers to abnormal spindles.

SPL-A induced multipolar spindles in the cells of both lines. At 1.25 µg/ml, 53.3% of SKOV-3 cells and 44.0% of OVCAR-3 cells have multipolar spindles, whereas the percentage of normal spindles drastically decreases.

Also, SPL-A induced various abnormal spindles at high concentrations. At 5 µg/ml, 56.7% of SKOV-3 cells had disorganized spindles with the highest percentage. At 2.5

μg/ml, 57.3% of OVCAR-3 cells had disorganized spindles with the highest percentage. The percentage of disorganized spindles decreased with increases in SPL-A concentration, and the percentage of multipolar spindles instead increased. The percentage of monopolar spindles increased by high doses of SPL-A.

Although not shown herein, γ-tubulin is localized at the poles of each spindle, whereas centrin-2 was detected only in those two. Further image analysis by time-lapse photography revealed that SPL-A selectively inhibits the nucleation of centrosomal microtubules, whereas centromere microtubules undergo nucleation and polymerization, resulting in the formation of ectopic spindle poles and multipolar spindles.

The results that SPL-A selectively disrupts the nucleation of centrosomal microtubules and induces multipolar spindles reproduce a TACC3 depletion phenotype that suppressed TACC3 expression using shRNA. In addition, OVCAR-3 was more highly sensitive than SKOV-3 to SPL-A treatment. This is consistent with previous observation in which TOGp depletion induces more severe spindle malfunction in OVCAR-3 than in SKOV-3.

The SPL treatment reproduces a spindle phenotype induced by TACC3 depletion or TOGp depletion. This suggests that SPL-A inhibits the TACC3-TOGp pathway and destabilizes spindle microtubules.

Example 8

Interaction Between TACC3-TOGp Complex and SPL

As mentioned above, the SPL treatment produced results similar to those about the suppression of TACC3 expression using shRNA or the suppression of TOGp expression, suggesting that SPL acts on spindle microtubules via a TACC3-TOGp complex. It was thus predicted that SPL might interact directly with the TACC3-TOGp complex. Thus, the complex was analyzed for its direct binding to SPL.

(1) Binding of SPL to TACC3 and TOGp

Immobilized SPL on agarose beads was prepared. A cell lysate of SKOV-3 was prepared by sonication in a binding buffer (10 mM Tris-HCl (pH 7.5), 50 mM KCl, 5 mM $MgCl_2$, 1 mM EDTA, and protease inhibitor mixtures (manufactured by F. Hoffmann-La Roche, Ltd.)). After removal of insoluble materials by centrifugation, the supernatant (500 μg of proteins) was incubated with 30 μl of the beads at 4° C. for 3 hours. The beads thus incubated were washed four times with a binding buffer containing 0.025% NP40. The proteins bound with the beads were eluted using an SDS-PAGE sample buffer, then separated by SDS-PAGE, and then transferred to nitrocellulose. The blot was incubated with primary antibodies, subsequently incubated with peroxidase-conjugated secondary antibodies, then visualized by use of ECL detection system (GE Healthcare Japan Corp.). An antibody against TACC3 or TOGp and as a control, antibody against GADPH were used.

The antibody against human TACC3 was produced by the immunization of rabbits with a peptide corresponding to amino acids 213 to 224 of human TACC3. The rabbit anti-TOGp antibody was produced against C-terminal 111 amino acids of human TOGp fused with GST protein. These antibodies were used after purification using peptide-bound immunoaffinity columns. The anti-GADPH antibody (sc-25778) was purchased from Santa Cruz Biotechnology, Inc.

(2) Results

Figure 6:
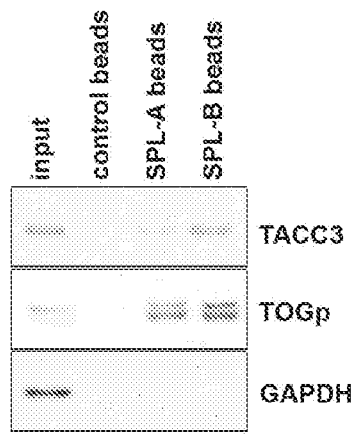
FIG. 6 Diagram showing the interaction between a TACC3-TOGp complex and SPL.

In FIG. 6, SPL-A beads, SPL-B beads, and control beads represent SPL-A-immobilized agarose beads, SPL-B-immobilized agarose beads, and unimmobilized agarose beads, respectively.

TACC3, TOGp, and GAPDH represent anti-TACC3 antibody, anti-TOGp antibody, and anti-GAPDH antibody treatments, respectively.

As shown in FIG. 6, the specific binding between SPL and TACC3 was observed. The signal intensity of TACC3 was stronger in SPL-B than in SPL-A. This is consistent with the higher activity of SPL-B in the cell growth inhibition assay. Also, coprecipitates were detected by immunoblotting using an anti-TOGp protein antibody. TOGp was detected from the SPL beads, indicating the interaction between the TACC3-TOGp complex and SPL.

Thus, SPL was shown to inhibit the spindle formation of microtubules via direct binding to the TACC3-TOGp complex to induce abnormal spindle morphology and cell division inhibition. These results indicate that SPL targets not only TACC3 but TOGp. Although only the results about SPL are shown herein, compounds having the common structure of the formula (I) is presumed to induce cell growth inhibition under a similar mechanism.

Example 9

In Vivo Antitumor Effect of SPL-B

Next, the ability of SPL to act as an anticancer agent is shown using an in vivo experimental system.

(1) Method

All animals and methods were approved by the Japanese Foundation for Cancer Research (JFCR, Japan) Cancer Institute Animal Committee. For xenograft tumor models, $1 \times 10^7$ cells of ovary cancer cells, SKOV-3 cells, were subcutaneously injected to both flanks of 9 NOD/SCID mice (Charles River Laboratories Japan, Inc.). When their tumor volumes reached approximately 200 $mm^3$, 50 μl of SPL-B dissolved in DMSO was orally administered to each mouse every 2 days. The tumor volumes were measured every 2 days. DMSO was administered as a control by the same procedure as above. Two or 3 mice were analyzed in each group. In this context, the tumor volumes were determined by measuring the length (L) and width (W) of each tumor using calipers and calculating the tumor volume (tumor volume=L×W×W/2).

Thirteen days after the treatment, the mice were dissected to collect tissues, which were then fixed overnight in 10% buffered formalin (Wako Pure Chemicals Industries, Ltd.,) and embedded in paraffin to prepare 1-, 4- or 6-μm sections. The sections were immunostained with anti-p53, anti-p21, anti-H3K9me3, and anti-PCNA antibodies. The percentage of positive cells in at least 10 regions arbitrarily selected in two sections was measured. The data was indicated by a mean and SD.

(2) Results

The start date of SPL-B administration is defined as day 1. The tumor volume at the start day of SPL-B administration is defined as 1.

Figure 7:
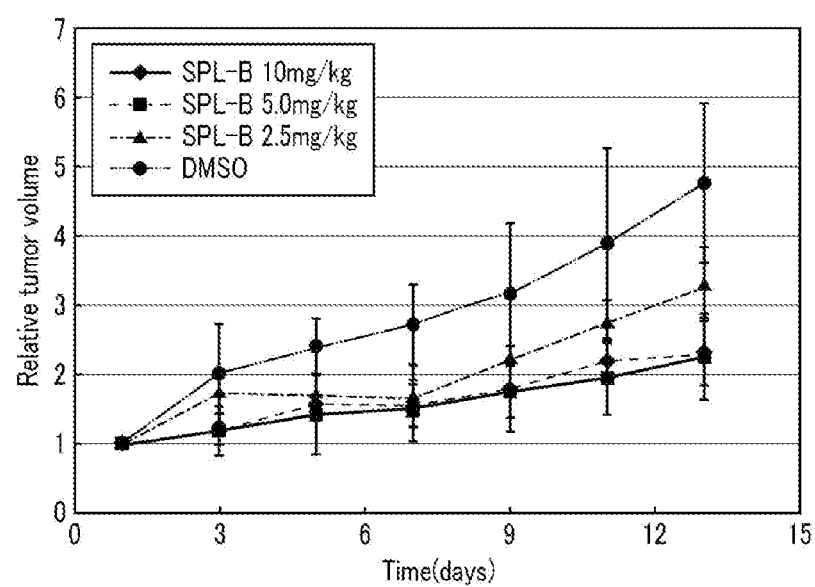
FIG. 7 Diagram showing the in vivo antitumor effect of SPL-B.

As shown in FIG. 7, SPL-B inhibited tumor growth in a dose-dependent manner in vivo.

In addition, SPL-B was orally or intraperitoneally administered at a dose of 20 mg/kg. Six hours after administration, its concentrations in serum were measured. As a result, the orally administered SPL-B showed a serum concentration of 270 ng/ml, whereas the intraperitoneally administered SPL-B showed a serum concentration of 90 ng/ml. Thus, SPL-B exhibits higher concentrations in blood by oral administration and has various clinical applicability for treatment.

Figure 8:
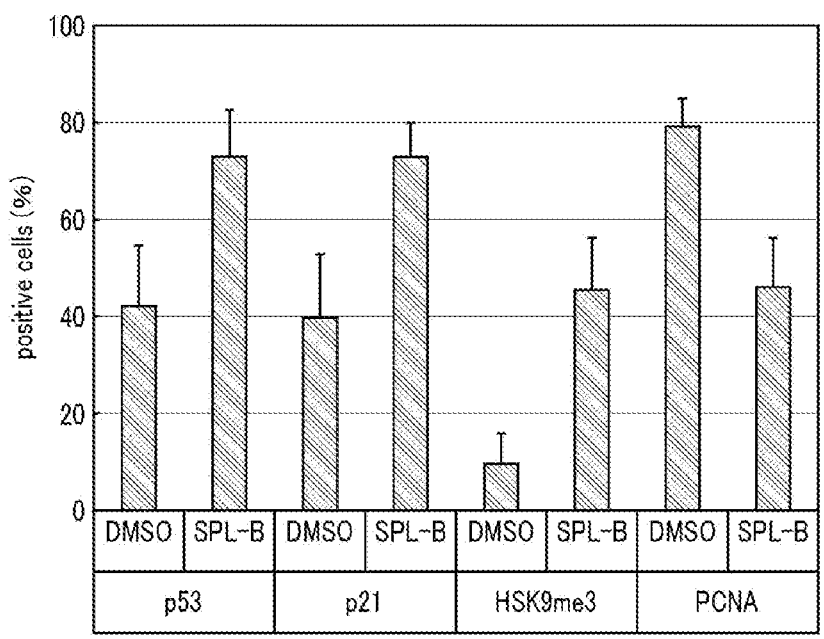
FIG. 8 Diagram showing the effect of SPL-B administration on tumors by immunohistochemical analysis. Tumor sections were immunohistologically stained using anti-p53, anti-p21, anti-H3K9me3, and anti-PCNA antibodies, and the percentage of positive cells is shown.

As shown in FIG. 8, the SPL-B treatment enhances the expression of p53, p21, and K9 trimethyl histone H3 (H3K9me3) which induce cell death and suppresses the expression of PCNA which induces cell growth. These results indicate that the anticancer effect of SPL-B is attributed to the activation of the p53-p21 pathway.

Example 10

Effect of SPL-B on Various Cell Lines

Provided that SPL acts on spindle formation and mitotic apparatus control via the TACC3-TOGp complex, SPL is considered to have a cell growth inhibitory effect on a wide range of cancer types. Thus, the effect of SPL was assayed using various cancer cell lines.

(1) Method

SPL-B was allowed to interact on cell lines of human cancer cell line panel (Non Patent Literature 14) and analyzed for the effects of SPL on cell division.

Figure 9:
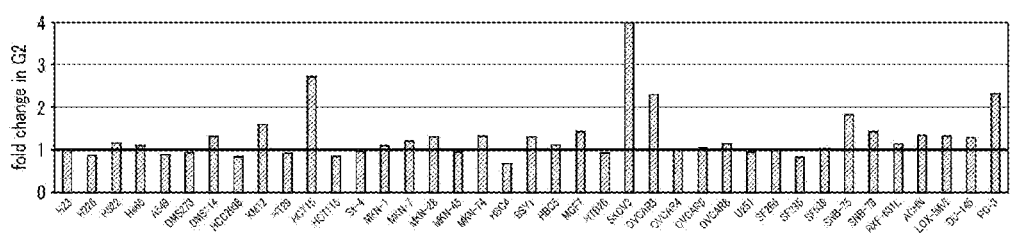
FIG. 9 Diagram showing results of analyzing the cell cycles of various cancer cell lines using after SPL-B treatment.

The cells were treated with SPL-B at a concentration of 0.5 μg/ml for 24 hours, then stained with propidium iodide (PI), and analyzed by flow cytometry. FIG. 9 shows the changes in G2/M-phase cells by the SPL-B treatment.

(2) Results

Among 39 cell lines used in the analysis, over half thereof (21 cell lines) exhibited increase in the percentage of G2/M-phase cells, demonstrating that SPL has the effect of arresting cell division. Particularly, the ovary cancer-derived cell lines SKOV-3 and OVCAR-3, the colon cancer-derived cell lines HCT15 and KM12, the glioma-derived cell lines SNB-75 and SNB-78, the prostate cancer-derived cell lines PC-3 and DU145, the kidney cancer-derived cell line ACHN, and the melanoma-derived cell line LOX-IMVI exhibited marked increase in the percentage of G2/M-phase cells, indicating the high cell division-arresting effect by SPL.

Example 11

Selective Growth Inhibitory Effect of SPL on Cancer Cell

Next, SPL, unlike other mitotic poisons or kinase inhibitors, is shown to cause no growth inhibition in normal cells, though being effective for the growth inhibiting of cancer cells.

Figure 10:
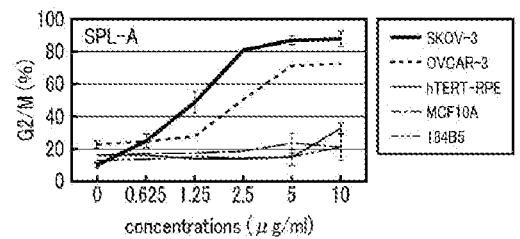
FIG. 10 Diagram showing results of analyzing the growth inhibitory effects of SPL-A and other anticancer agents on normal cells and cancer cells.
Figure 10:
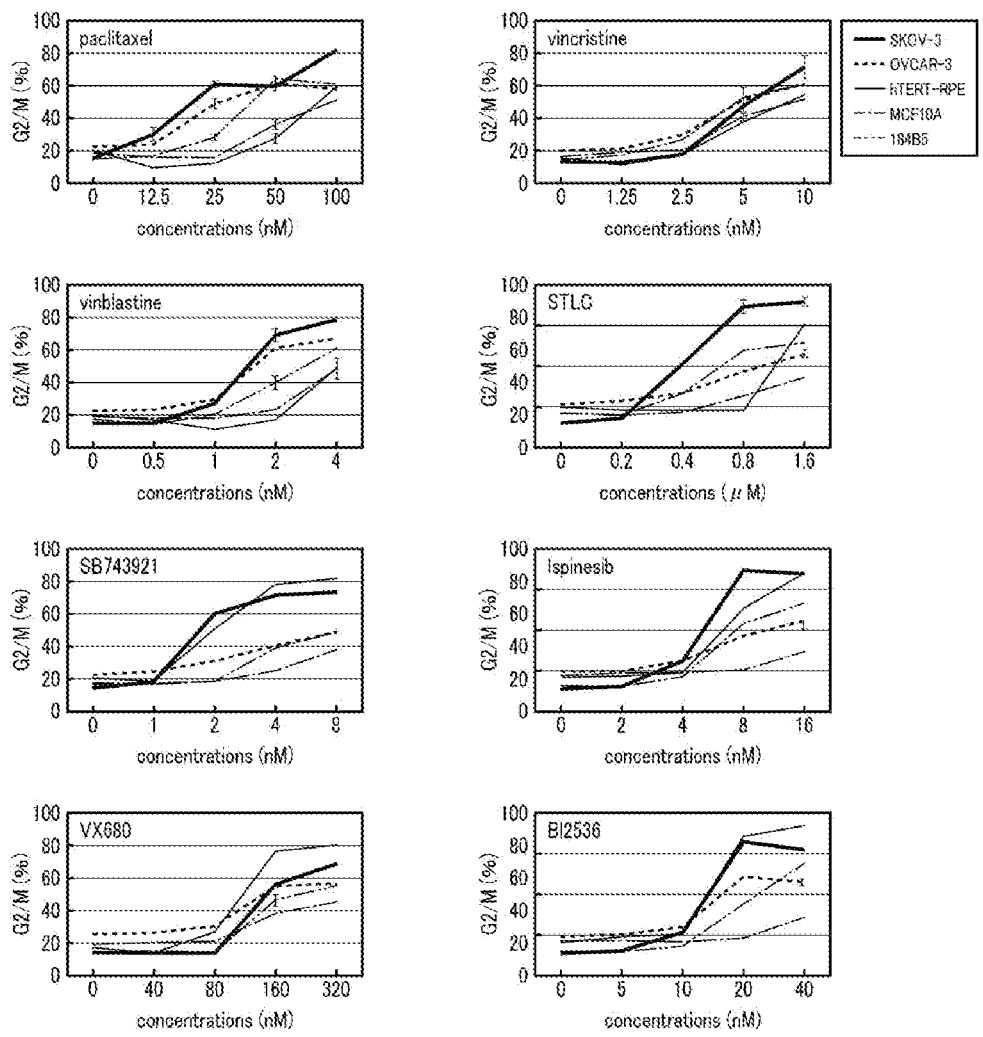

(1) Method (A) Two cancer cell lines SKOV-3 and OVCAR-3 and three normal cell lines hTERT-RPE, MCF10A, and 184B5 were treated with SPL-A at concentrations shown in the abscissa of FIG. 10A for 24 hours, then stained with propidium iodide (PI), and analyzed by flow cytometry. FIG. 10A shows the rate of changes in G2/M-phase cells by the SPL-B treatment.

(B) Agents known to act on spindle microtubules to inhibit tumor growth were analyzed for their effects.

The same two cancer cell lines and three normal cell lines as in (A) were treated with each of paclitaxel, vincristine, and vinblastine acting on microtubule formation, S-trityl-L-cysteine (STLC) and SB743921 acting on proteins involved in mitosis, an Aurora kinase inhibitor VX680, and a polo-like kinase (PLK) inhibitor BI2536 at concentrations shown in the abscissa of FIG. 10B for 24 hours, then stained with propidium iodide (PI), and analyzed by flow cytometry. FIG. 10B shows the rate of changes in G2/M-phase cells by the treatment with each agent.

(2) Results

As shown in FIG. 10A, SPL-A increased the percentage of G2/M-phase cells in a concentration-dependent manner in the two cancer cell lines and thus has the effect of arresting cell division. However, even at high concentrations SPL acts no inhibitory effect on cell division of the 3 normal cell lines. Thus, SPL-A was shown to selectively inhibit on cancer cells.

By contrast, all of other compounds or agents known to act on microtubular polymerization/depolymerization or spindle formation associated therewith inhibited the division of all the cell lines in a concentration-dependent manner and thus lack a selective effect on tumor cells as seen in SPL (FIG. 10B).

Thus, it was shown that the effect of inhibiting the division of cancer cells, but not acting on normal cells is unique to SPL, whereas other mitotic poisons or kinase inhibitors, etc. lack such properties. Since the compound of the present invention specifically acts on cancer cells but does not act on normal cells, the compound of the present invention used as an anticancer agent is likely to cause no serious adverse reaction.

Example 12

Effect Brought about by Combined Use of SPL and Additional Anticancer Agent

Figure 11:
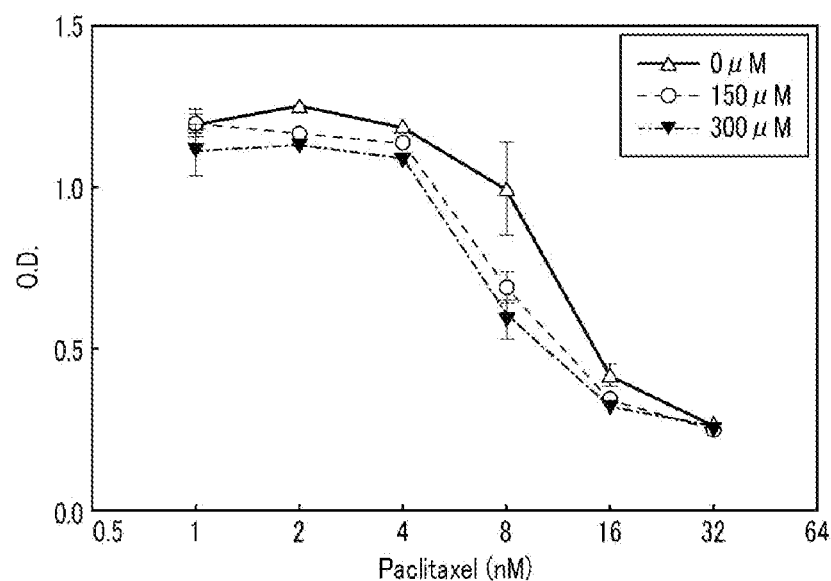
FIG. 11 Diagram showing effect on cancer cell growth by the combined use of SPL-B and paclitaxel.
Figure 11:
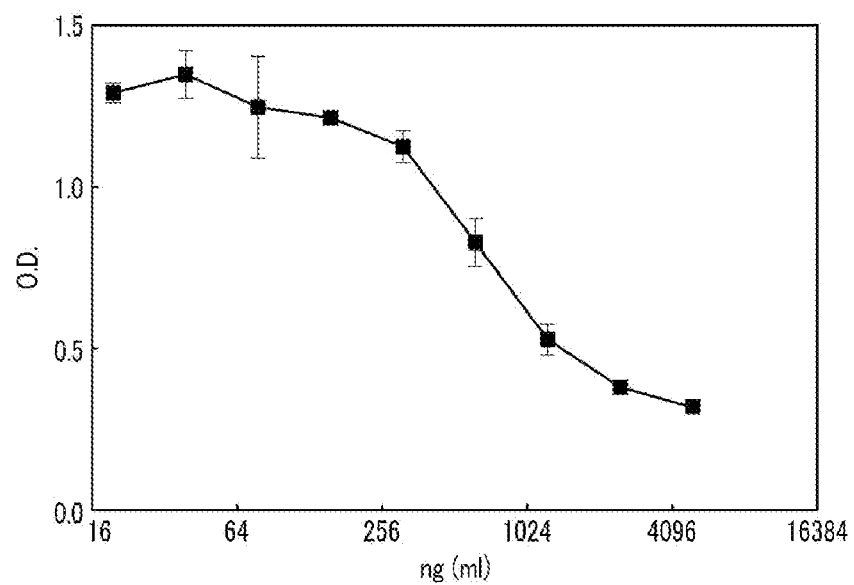

Next, effects brought about by combined use with an anticancer agent known in the art were studied. If the compound of the present invention used in combination with an additional agent has an enhancing effect, the dose of each agent can be decreased, resulting in reduced adverse reactions.

p53-knockout cells derived from human colon cancer cells HCT-116 were cultured after combined administration of paclitaxel and SPL-B. Three days after cultivation, the survival rate of the cells was measured by WST assay. The results are shown in FIG. 11.

FIG. 11A shows the results of measuring, by WST assay, the cell growth of the p53-knockout HCT-116 cells cultured with combined addition of SPL-B at concentrations of 0, 150, and 300 μM and paclitaxel in a concentration range of 0 to 32 nM. $IC_{50}$ of paclitaxel was 8.339 nM in the absence of SPL-B, 7.697 nM in the case of adding SPL-B at 150 μM, and 7.537 nM in the case of adding SPL-B at 300 μM.

As shown in FIG. 11B, SPL-B alone is rarely effective for cell growth even when added at 300 μM to the medium, whereas the combined use thereof with paclitaxel can enhance the cell growth inhibitory effect. Paclitaxel, a microtubular depolymerization inhibitor, inhibits cell division as with SPL-B. SPL-B, however, differs in the mechanism of action from paclitaxel and is therefore considered to have an enhancing effect. As shown above, the compound of the present invention is orally administrable and acts on spindles via TACC3 or a TACC3-TOGp complex without acting on microtubules themselves. Thus, the compound of the present invention does not inhibit the functions of microtubules even in non-dividing cells, unlike vinca alkaloids currently used as anticancer agents targeting microtubules. Accordingly, the compound of the present invention is free from serious adverse reactions such as peripheral neuropathy.

INDUSTRIAL APPLICABILITY

The present invention provides a novel anticancer agent targeting the TACC3 protein. The compound of the present invention acts on individuals through oral administration and inhibits the functions of spindles at low concentrations. The compound of the present invention can therefore be used as an anticancer agent with few adverse reactions.

The invention claimed is:
1. An anticancer agent comprising, as an active ingredient, a compound according to formula (i):

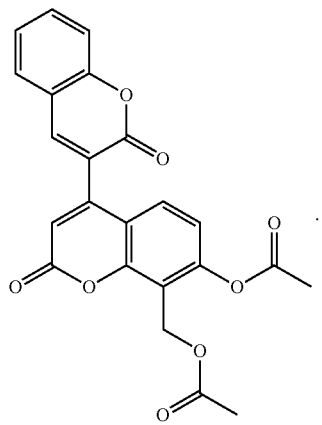 [SMILES: CC(=O)OCc1c(OC(C)=O)ccc2c(-c3cc4ccccc4oc3=O)cc(=O)oc12]

(i)

2. A compound represented by the following formula:

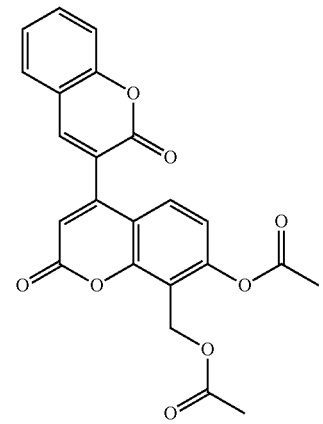

3. A method for treating cancer, targeting at TACC3 and/or TACC3-TOGp complex, comprising administering to a subject a therapeutically effective amount of a compound, wherein the compound is represented by the following formula:

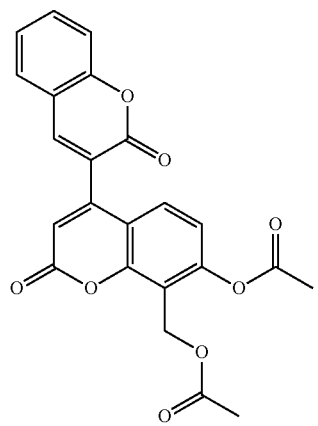

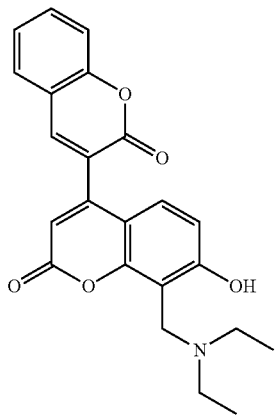

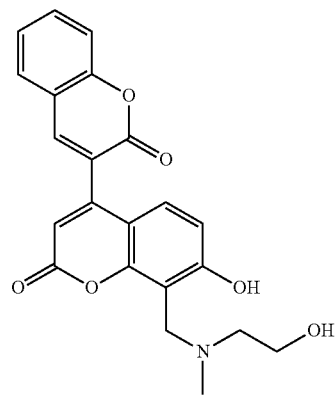

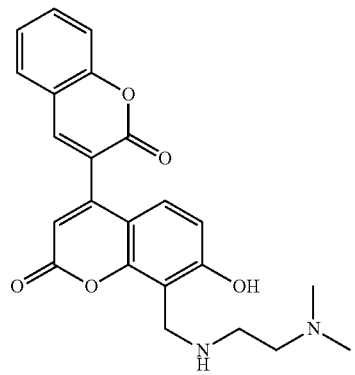

39
-continued
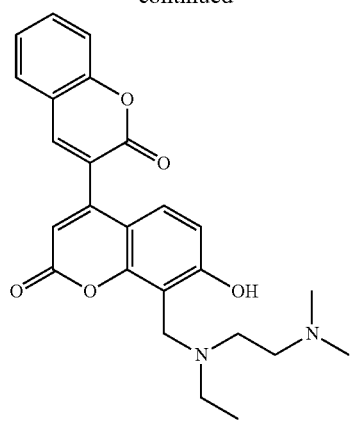
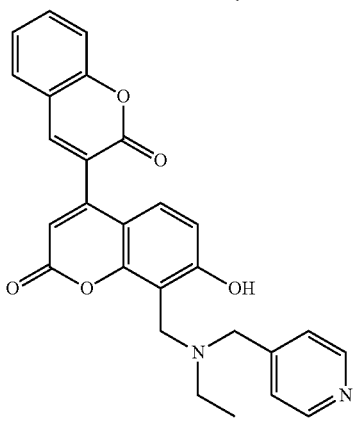
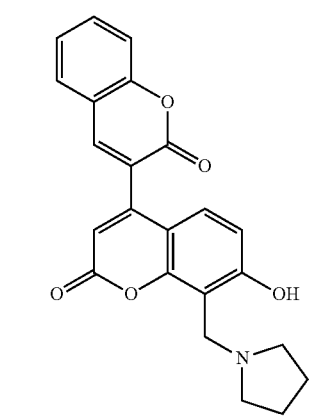
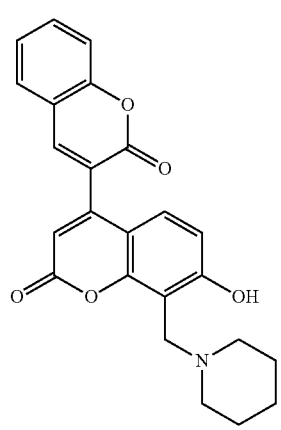
40
-continued
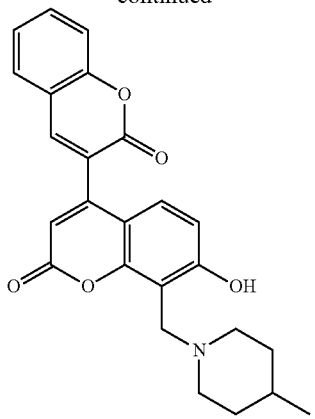
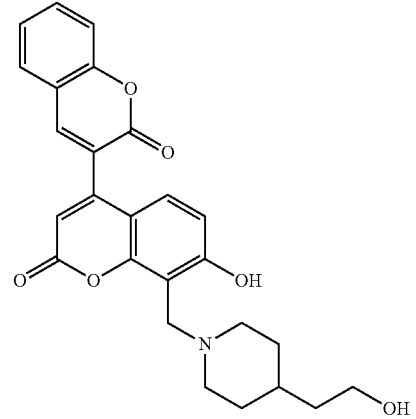
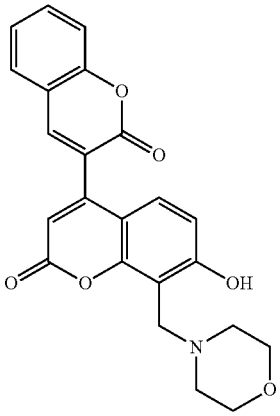
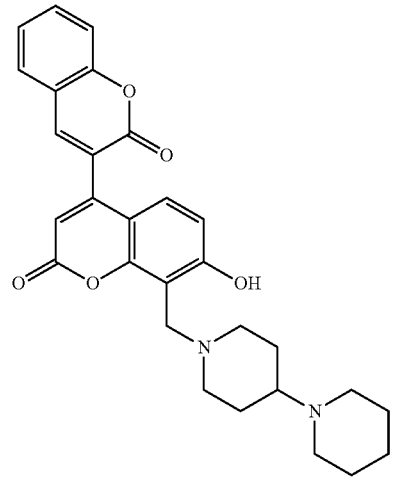

-continued

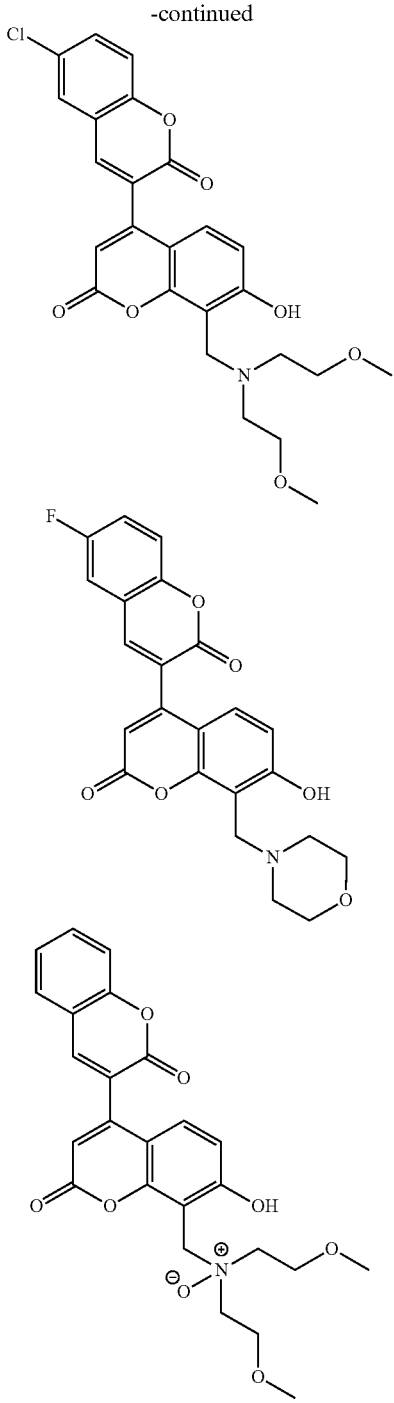

-continued

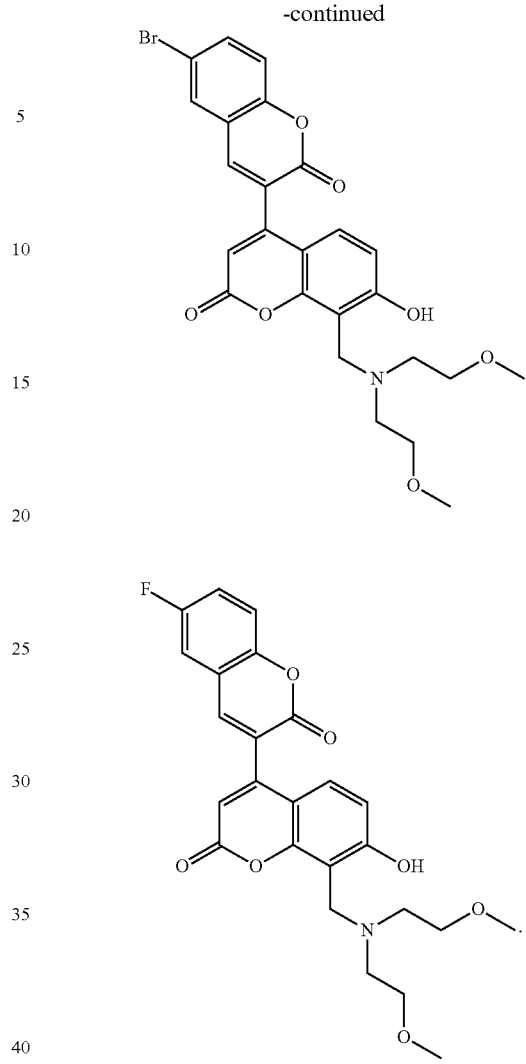

4. The anticancer agent according to claim 1, wherein the anticancer agent targets a cancer expressing TACC3.

5. The anticancer agent according to claim 4, wherein the targeted cancer expressing TACC3 is colon cancer, ovary cancer, uterine cancer, breast cancer, esophagus cancer, lymphoma, glioma, prostate cancer, kidney cancer, or melanoma.

6. The anticancer agent according to claim 1, wherein the anticancer agent is for oral administration.

\* \* \* \* \*